United States Patent
Thomas

(10) Patent No.: US 8,001,842 B2
(45) Date of Patent: *Aug. 23, 2011

(54) ULTRASONIC FAULT DETECTION SYSTEM USING A HIGH DYNAMIC RANGE ANALOG TO DIGITAL CONVERSION SYSTEM

(75) Inventor: Andrew Robert Thomas, Westford, MA (US)

(73) Assignee: Olympus NDT, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/411,088

(22) Filed: Mar. 25, 2009

(65) Prior Publication Data
US 2009/0178485 A1    Jul. 16, 2009

Related U.S. Application Data

(63) Continuation of application No. 11/489,889, filed on Jul. 20, 2006.

(51) Int. Cl.
*G01N 29/04* (2006.01)
(52) U.S. Cl. .............. 73/602; 73/629; 73/627; 73/631
(58) Field of Classification Search .............. 73/602
See application file for complete search history.

(56) References Cited

U.S. PATENT DOCUMENTS

| | | | | |
|---|---|---|---|---|
| 4,170,143 A | * | 10/1979 | Ries et al. | 73/609 |
| 4,364,274 A | * | 12/1982 | Sharpe | 73/615 |
| 4,446,737 A | * | 5/1984 | Hottier | 73/602 |
| 4,809,184 A | * | 2/1989 | O'Donnell et al. | 600/437 |
| 5,671,154 A | * | 9/1997 | Iizuka et al. | 73/602 |
| 6,358,205 B1 | * | 3/2002 | Ustuner et al. | 600/437 |
| 7,506,546 B2 | * | 3/2009 | Cuffe et al. | 73/602 |
| 2004/0000841 A1 | * | 1/2004 | Phelps et al. | 310/314 |
| 2005/0251041 A1 | * | 11/2005 | Moehring | 600/441 |

FOREIGN PATENT DOCUMENTS

| JP | 02245921 A | * | 10/1990 |
|---|---|---|---|
| JP | 02246943 A | * | 10/1990 |

* cited by examiner

*Primary Examiner* — Hezron E. Williams
*Assistant Examiner* — Nashmiya Fayyaz
(74) *Attorney, Agent, or Firm* — Ostrolenk Faber LLP

(57) ABSTRACT

A method and apparatus for effecting ultrasonic flaw detection of an object processes an echo signal received from the object being tested in at least three signal channels, wherein the echo signal is scaled to different degrees along each channel to increase and extend the dynamic range of an associated A/D converter system, in a manner which dispenses with the need for using numerous analog high pass and low pass filters and a variable gain amplifier. This reduces complexity and avoids performance limitations. The digital to analog converters sample the differently scaled input signal and a selection circuit selects the output of the digital output obtained from that analog to digital converter which has the highest gain, but which has not overflowed. The digital outputs are seamlessly merged to produce an output that can be displayed as a scan display which shows the location of faults.

18 Claims, 18 Drawing Sheets

ULTRASONIC FAULT DETECTION SYSTEM USING A HIGH DYNAMIC RANGE ANALOG TO DIGITAL CONVERSION SYSTEM

CROSS-REFERENCE TO RELATED APPLICATIONS

This application claims the benefit and priority of U.S. patent application Ser. No. 11/489,889 filed Jul. 20, 2006 entitled ULTRASONIC FAULT DETECTION SYSTEM USING A HIGH DYNAMIC RANGE ANALOG TO DIGITAL CONVERSION SYSTEM and U.S. Provisional patent application Ser. No. 60/726,798 filed Oct. 14, 2005 entitled ULTRASONIC FAULT DETECTION SYSTEM USING A HIGH DYNAMIC RANGE ANALOG TO DIGITAL CONVERSION SYSTEM and U.S. Provisional patent application Ser. No. 60/726,776, filed Oct. 14, 2005 entitled ULTRASONIC DETECTION MEASUREMENT SYSTEM USING A TUNABLE DIGITAL FILTER WITH 4× INTERPOLATOR, and U.S. Provisional patent application Ser. No. 60/726,575, filed Oct. 14, 2005 entitled DIGITAL TIME VARIABLE AMPLIFIER FOR NON-DESTRUCTIVE TEST INSTRUMENT, the entire disclosures of which are incorporated herein by reference.

BACKGROUND OF THE INVENTION

The present invention generally relates to ultrasonic inspection systems utilized to detect internal structural faults, e.g. cracks, discontinuities, corrosion or thickness variations within an object or a material, for example, in such crucial structures as airline wings. This is done by transmitting ultrasonic pulses to a target object and analyzing echo signals detected from the target object. More particularly, the present invention relates to a high dynamic range analog to digital conversion system and method which can be used in such ultrasonic inspection systems, particularly whereby the object is scanned with an ultrasonic probe or transducer. The present invention also relates to eddy current inspection systems utilized to detect internal structural faults.

The prior art of ultrasonic flaw detectors is exemplified by such products as the instant assignee's Epoch 4 Plus product. Competitive products available from General Electric are known as the USM 35X, USN 58L and USN 60 fault detection systems. In general, prior art ultrasonic flaw detectors utilize highly complex analog front ends that contain many parts which pose especially difficult problems in terms of calibration, reliability, set up time, consistency of results and optimization for specific usages and settings.

Typical prior art ultrasonic flaw detectors include a transducer which is placed against the object to be tested and which works in conjunction with numerous analog circuits such as gain calibrators, preamplifiers and attenuators, variable gain amplifiers, and high pass and low pass analog filters that operate over many different frequency bands and which need to be carefully calibrated and maintained.

As a result, present flaw detectors present a host of problems to designers and users of such equipment, which impact their troubleshooting and repair owing to their complexity. These problems include such issues as matching input impedances seen by the transducer which changes with different gain amplifiers that are switched in and out of the signal path. This adversely impacts the frequency response and introduces various gain nonlinearities. It poses issues of calibration, as analog circuits are switched in and out of the signal path.

Another problem with existing flaw detectors is attributable to their back wall attenuation performance which impacts the ability to detect flaws that are located very near the back wall of the object being tested. This problem poses particular problems with the time varied gain function which has a limited gain range and gain rate of change in prior art devices.

Another prior art drawback ensues from the manner in which analog circuits are coupled, which results in each operational amplifier in the signal path having different DC offset errors that must be nulled in order to keep the input signal at the mid-point of the analog to digital converter being utilized, in order to allow the maximum full amplitude scale of such converter to be utilized. Furthermore, the DC offset errors can cause the waveform presented on the display to not be centered vertically on the waveform portion of the screen, thereby causing an undesirable anomaly in the waveform that the operator analyzes to determine the results of their inspection. The error nulling processes in the prior art are therefore unreliable, particularly at high gain, due to DC baseline measurement inaccuracies caused by noise.

The intensely analog implementation of the front ends of existing flaw detectors poses further issues owing to the need to utilize the entire dynamic range of the instrument to be utilized which creates various gain linearity calibration issues.

An ultrasonic inspection apparatus of the prior art is described in U.S. Pat. No. 5,671,154, which provides background information for the apparatus and method of the present invention.

SUMMARY OF THE INVENTION

Generally, it is an object of the present invention to provide an apparatus and method for ultrasonic inspection of objects which avoid or ameliorate the aforementioned drawbacks of the prior art.

It is a further object of the invention to provide an ultrasonic inspection apparatus and method that is implemented in simpler circuitry.

It is a further object of the present invention to provide an ultrasonic inspection apparatus and method that requires a shorter and simpler process of calibration and adjustment prior to use.

Yet another object of the invention is to provide an ultrasonic inspection apparatus and method that provides an electronic inspection apparatus and method that delivers more accurate and more easily readable and consistent inspection results.

The foregoing and other objects of the invention are realized by a method and apparatus that extend the dynamic range of the A/D converter circuit and eliminate the need for a Variable Gain Amplifier (VGA) circuit and its associated complexity and performance limitations.

According to one aspect of the invention, the apparatus and method of the invention are embodied as a multiple A/D circuit that includes multiple channels coupled to receive a single analog input signal, each of the channels having the means for converting the analog input signal to a digital signal.

Another aspect of the invention includes: a means to adjust the respective sample times to compensate for all sources of timing skew, including the propagation delays of each preamplifier and any other source of skew revealed by examination of the A/D converter output data; a means for preventing saturation of the input stage of each channel's preamplifier to prevent signal distortion from affecting the inputs to the other channels; a means for adjusting the frequency response of each channel to substantially match, as well as adjusting the overall frequency response of the apparatus; a means for detecting a channel overflow condition in one or more of the channels having higher gain; and a means for merging the multiple channels into a continuous output stream.

According to another aspect of the invention, the multi-channel converter circuit of the invention includes a means for eliminating signal offset errors in each channel by injecting DC signals from a D/A converter at various points of the analog signal path to null out the offset errors.

According to another aspect of the invention, the means for merging the multiple channels is operable as a function of a result generated by the channel overflow condition detection means. Furthermore, the means for merging the multiple channels is operable to output a result of the channel having lower gain when a channel overflow condition is detected on any of the channels having higher gain.

According to another aspect of the invention, the means for substantially matching the frequency response of each analog channel is provided to minimize amplitude matching errors between channels, particularly at high frequencies.

According to another aspect of the invention, each A/D converter circuit includes a means for changing the reference voltage to adjust the full scale range by using a D/A converter. This is used to optimize signal amplitude matching.

According to another aspect of the invention, the multiple A/D converter circuit of the invention includes a means for matching the result of each channel with different gains.

According to another aspect of the invention, the multiple A/D circuit of the invention also includes a means for adjusting placement of the rising edge of the sample clock of one channel in time with respect to a clock circuit portion of another channel so that the sample times of each channel are adjusted to compensate for the propagation delays of each preamplifier channel and any other source of skew revealed by examination of the A/D converter output data.

According to another aspect of the invention, the channel overflow condition detecting means further comprises a means to extend the time duration of the overflow signal that comes from the A/D converters in order to ensure that all amplifiers in the signal path from the first amplifier to the amplifiers internal to the A/D converters have adequate time to return to their linear region of operation.

According to still another aspect of the invention, the means for merging multiple channels further comprises a means for adjusting, e.g. scaling, a data bit position of a result of a channel, or channels, having lower gain to match a result of the channel, or channels, having higher gain. This can be accomplished, for example, by bit shifting using a shift register, a multiplexer and the like, or by any means.

According to yet other aspect of the invention, methods for converting an analog signal to a digital signal are provided which include, for example, splitting an input analog signal into larger and smaller signal channels; scaling the input signal on the larger and smaller signal channels such that the smaller signal channels have higher resolution than the larger signal channels; sampling the larger and smaller signal channels using separate A/D converters; and outputting the result of one of the larger and smaller signal channels as a function of determining whether the larger signal channel is valid.

The methods of the invention also include merging the results of the larger signal channels with the results of the smaller signal channels into a merged result; and outputting the merged results.

Other features and advantages of the present invention will become apparent from the following description of the invention which refers to the accompanying drawings.

DETAILED DESCRIPTION OF PREFERRED EMBODIMENTS OF THE INVENTION

Figure 1:
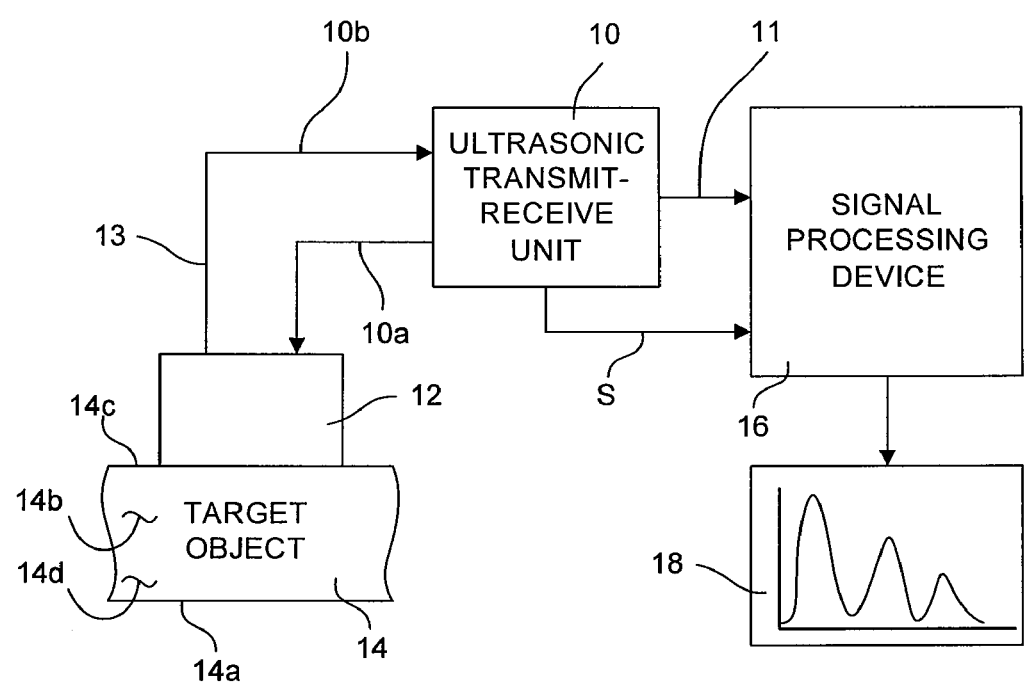
FIG. 1 is block diagram of a basic arrangement of an ultrasonic inspection apparatus.
Figure 2:
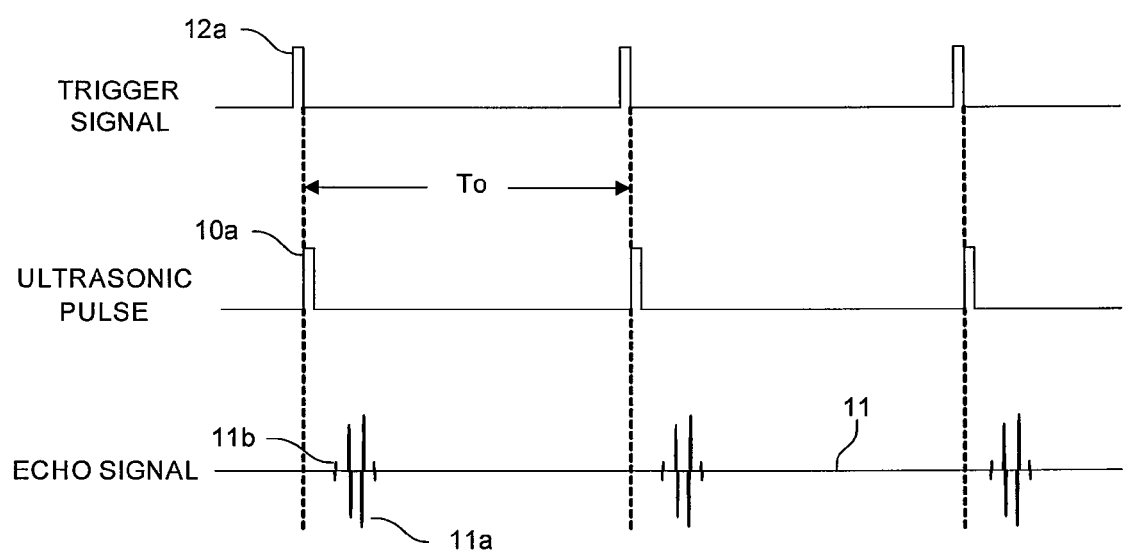
FIG. 2 is a basic waveform diagram for the device of FIG. 1.

Reference is initially made to FIGS. 1 and 2, to provide background information on the general environment of and various problems solved by the present invention.

In FIG. 1, an ultrasonic transmit-receive unit 10 transmits an electrical pulse signal 10a at a predetermined period to a probe or transducer 12 which is coupled to a target object 14, such as to steel material, directly or through a delay material such as water or quartz. As shown in FIG. 2, the probe 12 converts the trigger pulse signal 12a into an ultrasonic pulse 10a which it transmits through the target object 14. The ultrasonic pulse 10a applied into the target object 14 is subsequently reflected by a bottom surface 14a of the target object 14 and received by the probe 12. The probe 12 converts the reflected wave into an electrical signal which is supplied as an electrical echo signal 10b to the ultrasonic transmit-receive unit 10. The ultrasonic transmit-receive unit 10 amplifies the electrical signal 10b and transmits the amplified signal 11 to a signal processing device 16 as an echo signal 11. As used herein, the term probe or transducer includes embodiments which implement the transducer using distinct transmitter(s) and receiver(s).

The echo signal 11 includes a bottom surface echo 11a corresponding to the wave reflected by the bottom surface 14a and a flaw echo 11b caused by a flaw 14b in the object 14.

In addition, the frequency of the ultrasonic echo pulse 11 is determined primarily by the thickness or other property of the ultrasonic vibrator incorporated in the probe 12. The frequency of the ultrasonic pulse 10a used for inspection is set to tens of kHz to tens of MHz. Therefore, the frequency range of the signal waveforms of the bottom surface echo 11a, and the flaw echo 11b included in the echo signal 11 cover a wide range of from about 50 KHz to tens of MHz.

The signal processing device 16 performs various signal processing of the echo signal 11 received from the ultrasonic transmit-receive unit 10, and the signal processing device 16 displays on a display unit 18, an output result that represents the presence/absence of a flaw or flaws and in some cases, the thickness of the target object 14. In order to signal process the echo signal 11 and display the echo signal, a trigger signal S synchronized with the pulse signal 10a is supplied from the ultrasonic transmit-receive unit 10 to the signal processing device 16.

In the flaw inspection apparatus arranged as described above, the echo signal 11 output from the ultrasonic transmit-receive unit 10 includes, in addition to the bottom surface echo 11a and flaw echo 11b, a certain amount of noise. When the amount of noise included in the ultrasonic pulse 11 is large, the reliability of an inspection result is considerably degraded. The noise is roughly classified into electrical noise and material noise.

The electrical noise comprises external noise caused by mixing an electromagnetic or electrostatic wave into the probe 12, the ultrasonic transmit-receive unit 10, connection cables, e.g., cables 13, or the like, and internal noise generated by amplifier(s) and the like incorporated in the ultrasonic transmit-receive unit 10.

Reduction of the noise included in the echo signal 11 is very important to perform ultrasonic inspection at high accuracy. Conventionally, an analog filter is used to reduce noise components included in the echo signal 11. For example, a BPF (Band pass Filter) is used to pass the frequency component of the ultrasonic echo relative to the electrical noise having a wide-frequency component. In addition, an LPF (Low-Pass Filter) or a BPF is used for material noise, recognizing that the frequency distribution of the flaw echo 11b (FIG. 2) is lower than that of the echo produced by signal scattering. In this manner, when an analog filter is used, noise components included in the echo signal 11b can be reduced to a level equal to or lower than a predetermined level.

It is generally known that the frequency distribution of a flaw echo signal changes based on the ultrasonic attenuation characteristics of the target object 14. Therefore, when a BPF is to be used for material noise represented by a scattered echo or the like, a filter having optimal characteristics is desirably used in accordance with the target object 14. However, since the passing frequency characteristic of the analog filter cannot be easily changed, a larger number of filters, having different passing frequency characteristics corresponding to the different ultrasonic attenuation characteristics of the various materials associated with target objects 14 must be prepared. In this manner, when different filters are used in accordance with the material characteristics of target object 14, practical difficulties occur in consideration of operability or economic advantages versus the cost and complexity of the overall system.

In some cases, the flaw echo 11b may be very close to the front surface 14c of target object 14 which will place it in close proximity to the trailing edge of transmitted pulse 10a. For this reason, it is desirable for the end of the trailing edge (magnified as trailing edge 10at in FIG. 3) of the transmitted pulse 10a to settle to the zero base line 10ab as quickly as possible in order not to interfere with the returning flaw echo 11b. The settling time 7a to the zero base line is a determining factor of a flaw detector's near surface resolution.

Considering that the gain of the ultrasonic transmit-receive unit 10 can be adjusted up to 110 dB (as required by European standard EN 12668-1), a small amount of base line error prior to a gain amplification stage in the ultrasonic transmit-receive unit 10 will cause a large error at the output of the gain amplification stage if the gain level is set too high.

The resulting base line error at the input to the signal processing device 16 will either:

(a) cause the dynamic range to be reduced because the maximum vertical displacement of the signal on the screen will be reduced by the amount of offset of the base line, which produces a reduction in the instrument's sensitivity to detecting flaw echoes, or (b) if sufficiently high in amplitude, cause a gain amplification stage, or gain amplification stages, to saturate, thereby preventing an echo signal from being detected at all.

Conventionally, the base line error problem described above is addressed in one of two ways. In accordance with a first approach, a HPF is used in the signal path of the input of ultrasonic transmit-receive unit 10 in order to filter out the low frequency content of the trailing edge 10at of the transmitted pulse 10a. The trailing edge 10at of the transmitted pulse 10a can be improved by the HPF as is indicated by the approximated dotted line 7c.

However, the effectiveness of the HPF solution is limited in several manners. First, the HPF cutoff frequency (fHPF −3 dB) must be as high as possible to minimize the low frequency content of the trailing edge 10at of the transmitted pulse 10a. For example, if the excitation frequency of probe 12 is 10 MHz and the fHPF −3 dB is 5 MHz, the undesirable effect on the receiver base line is greatly reduced.

Unfortunately, it is not uncommon to use an excitation frequency for probe 12 as low as 500 kHz which would require the fHPF −3 dB to be below 500 kHz. The HPF solution loses much of its effectiveness in this frequency range because an undesirable amount of the low frequency content of the trailing edge 10at of the transmitted pulse 10a is allowed to pass through the HPF and contribute to base line error.

Secondly, the maximum amplitude of the transmitted pulse applied to a first amplifier stage (not shown) of ultrasonic transmit-receive unit 10 is limited (clamped) to a few volts in order to prevent damage to the amplifier circuit. It is common to operate the gain of the ultrasonic transmit-receive unit 10 at a level that will cause the amplifiers to saturate every time the pulser is fired. If the filters are not critically damped, the filter response after coming out of saturation will cause the trailing edge of the transmitted pulse 10a to be worse than if no filtering was applied. It is possible for each manufactured instrument to have the numerous filters tuned to ensure critical damping; however, practical difficulties occur in consideration of manufacturability and temperature drift of the filter components.

It should also be noted that once an amplifier goes into saturation, it takes a significant amount of time for the amplifier to return to the linear region of operation. This causes the trailing edge of the transmitted pulse 10a to take more time to return to the zero base line than would be the case if the amplifier input signal remained below the saturation level (i.e. within the linear range of operation).

An alternate method used to address the base line error problem is to directly couple the clamped transmitted pulse 10a to the input of ultrasonic transmit-receive unit 10. This method avoids one of the problems described above, because no HPF or BPF filters are used.

The effectiveness of the direct coupling solution is limited in two ways. First, it does nothing to reduce the low frequency content of the trailing edge 10at of the transmitted pulse 10a. Secondly, the DC component of the base line error and the offset errors of the amplifiers of the ultrasonic transmit-receive unit 10 pass through the signal path and are amplified. This can cause various dynamic range and saturation problems described further on.

Conventionally, flaw detectors have provisions that allow the user to operate the instrument either with filters or through direct coupling in order to select the optimal setting for the flaw measurement scenario.

Figure 4:
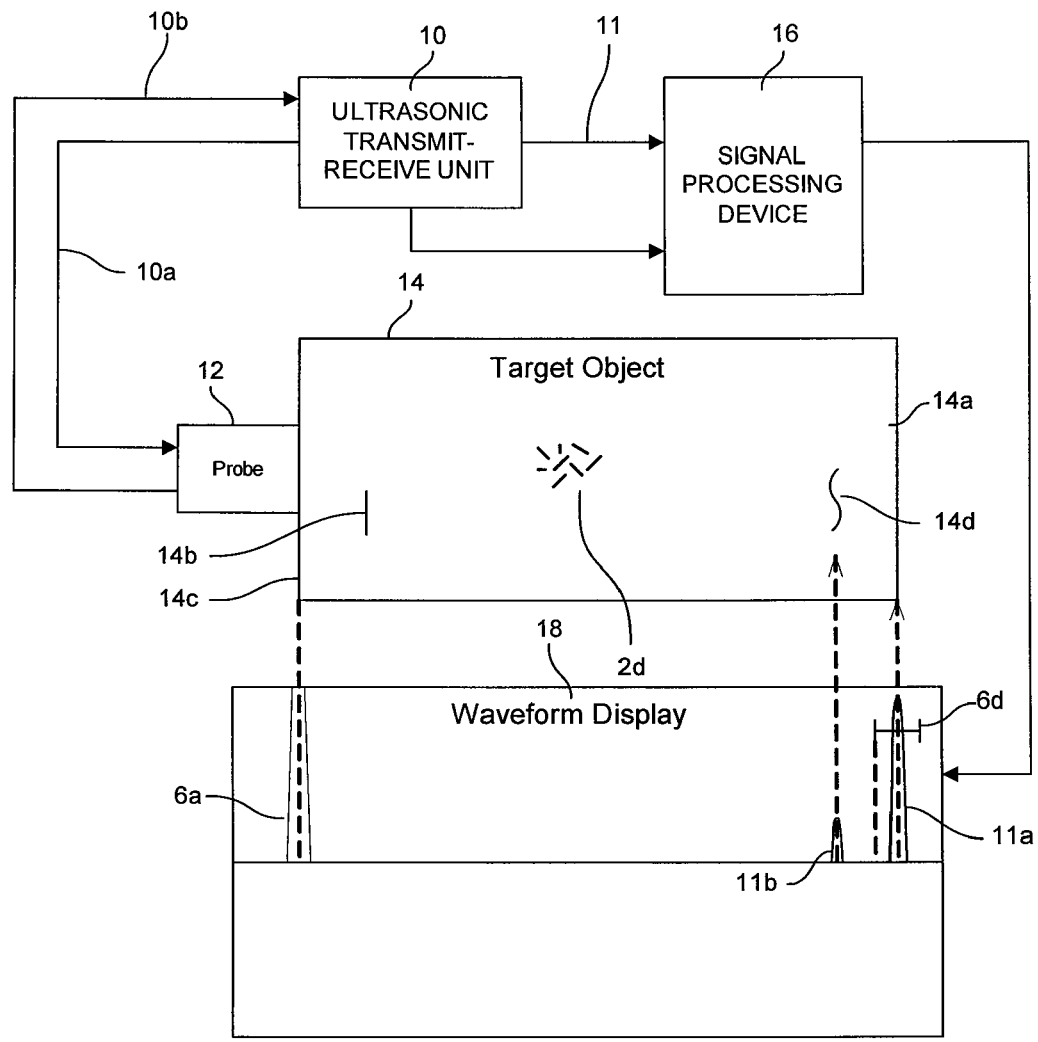
FIG. 4 is a block diagram that provides a side-by-side comparison of a waveform display with fault locations in a target object.

Reference is now made to FIG. 4 to describe detection of flaws near the rear surface of the object 14. In some cases, a flaw 14d may be very close to far surface 14a of target object 14 which will place the flaw echo 11b in close proximity to back wall echo 11a. In order to perform a proper inspection (in accordance with many formal inspection procedures), the peak of back wall echo 11a must remain visible on the waveform display 18 at all times. The reasons for this are: 1) small flaws 2d in target object 14 caused by porosity or material contaminants may generate flaw echoes that are not large enough to be seen on the waveform display 18, but may reduce the amplitude of the echo traveling to back wall 14a, thereby causing the amplitude of flaw echo 11b and back wall echo 11a to be reduced, and 2) probe 12 may be improperly coupled to the surface 14c of target object 14 intermittently, thereby reducing the amplitude of back wall echo 11a. These two conditions may cause the echo of flaw 14d to not be visible on the waveform display 18. However, the reduction in back wall echo 11a will indicate a problem with the target object 14 material or the coupling of probe 12. If the peak of back wall echo 11a was allowed to go beyond the top visible portion of the waveform display 18, a reduction in peak amplitude may not be visible on waveform display 18. The person performing the inspection sets up the back wall echo 11a detection parameters by adjusting back wall echo gate 6d (see FIG. 4) to set the region on the horizontal time axis where the back wall echo 11a is permissible. A threshold on the vertical amplitude axis is also set for the minimum acceptable echo amplitude. Typically, an alarm will occur when back wall echo 11a falls out of these parameters.

This measurement method produces certain problems.

The difference in echo amplitude between the flaw echo 11b and back wall echo 11a can be huge (as much as several orders of magnitude). But several methods described below (a, b, c and d) can be used to ensure that flaw echo 11b and the peak of back wall echo 11a both remain visible on waveform display 18:

(a) Connect probe 12 to two parallel receiver and A/D converter channels (A and B). The gain of channel A is adjusted by the person performing the inspection to optimize the amplitude of the echo of flaw 14d to make it is clearly visible on waveform display 18. The gain of channel B is adjusted to ensure that the peak of back wall 11a echo remains visible on waveform display 18 for the reason previously described.

The digital outputs of the channels A and B A/D converters are combined in such a way that the entire horizontal time scale of waveform display 18 shows all of the output of the channel A except for the region of back wall echo gate 6d. The leftmost side of back wall echo gate 6d indicates the point in time when the switch over from channel A to channel B would occur.

Unfortunately, the two channel method has disadvantages. Typically, an inspection is performed by moving probe 12 along the surface of target object 14 in a scanning motion because the presence or location of a flaw inside of the target object is not known until it is detected. If the target object does not have a constant thickness between front surface 14c and back surface 14a in the scanning area, the back wall echo gate 6d will need to be adjusted wide enough to include this variation in thickness in order not to miss the detection of back wall echo 11a.

Consequently, near back wall flaw echo 11b will not be detected if it is very close to back surface 14a because back wall flaw echo 11b will occur within the region of back wall echo gate 6d. This causes an undesirable effect on near surface resolution by far surface 14a. Further, the amount of receiver hardware is approximately twice as much as is required for a single channel solution.

(b) The two successive pulse-receive measurement cycles method is similar in concept to the two parallel receivers and A/D converter channels method except only one channel is required. The description in section (a) above applies to the two successive pulse-receive measurement cycles method. Also, instead of processing the flaw echo 11b and back wall echo 11a in two parallel channels set to different gains, the echoes are processed in the same channel, one pulse-receive cycle after the other, but with a different gain for each cycle.

A disadvantage that is unique to the successive pulse-receive measurement cycles method is that flaw echo 11b is separated in time from back wall echo 11a by an additional pulse interval To (shown in FIG. 2). Therefore, measurement errors are more likely to occur when probe 12 is moved because its location may change between the time that flaw echo 11b and back wall echo 11a are measured.

(c) Time varied gain (TVG) is a single channel solution wherein the gain of the amplifiers of the ultrasonic transmit-receive unit 10 is dynamically changed to optimize the amplitude of flaw echo 11b and back wall echo 11a (for the reason already described).

The TVG method has the same disadvantage for near surface resolution by far surface 14a as the two parallel receiver and A/D converter channels method does.

Figure 5:
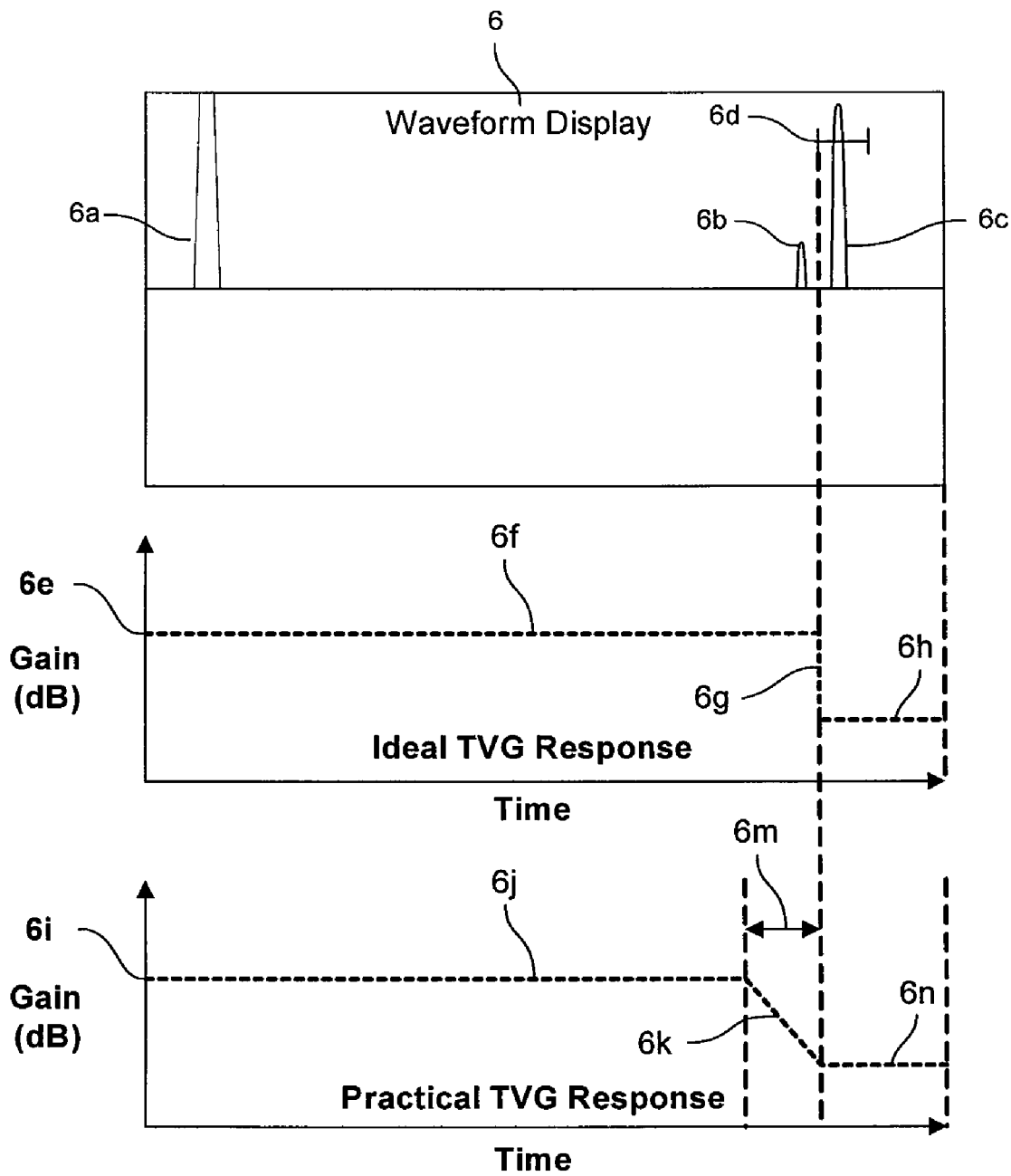
FIG. 5 is a continuation of FIG. 4.

But there are other disadvantages associated with the TVG method. Thus, FIG. 5 shows an ideal TVG curve 6e that changes instantaneously from gain 6f to gain 6h, thereby introducing no additional near surface resolution error from the analog TVG amplifier. The error associated with measuring a flaw near the back wall of a target object with non-constant thickness, as described in method a above, would still remain.

Unfortunately, it is impossible for analog TVG amplifiers to achieve the ideal curve 6e (especially, the instantaneous slope 6g). Analog TVG amplifiers and the external signals that control them have response times that limit gain rate of change 6g, thereby causing an undesirable effect on the near surface resolution by far surface 14a. The near surface resolution degrades because flaw 14d must be farther away from rear surface 14c of target object 14 in order to provide time interval 6m for the gain to change. Stated in terms of the echoes of interest, flaw echo 11b must occur before the start of time interval 6m, and back wall echo 11a must not occur before the end of time interval 6m.

The other problem associated with the TVG method is caused by the various sources of DC offset errors in the receiver section of ultrasonic transmit-receive unit 10. The sources include the input DC offset errors of the amplifier IC's and the DC component of the base line error.

The DC offset errors present in certain existing flaw detectors of the present assignee are compensated for at each gain setting every time the gain is adjusted from one level to the next. The DC offset errors are compensated for in this way to take into account the effects of temperature, and long term stability, drift on the DC offset errors, etc. The compensation method uses several D/A converters along the receiver signal path to inject a DC null signal that will ensure that the base line remains on the center of the A/D converter's full scale range and in an optimal location on waveform display 18. Every time the instrument is turned on, or the gain setting is changed, an algorithm runs in a microprocessor that takes a base line error reading, calculates the DC error correction value required, and sets the DACs to this value.

It is not practical to perform the DC offset compensation method described above for every gain setting at the speed that the TVG is required to operate at. Instead, the DC offset correction is set for the midpoint gain, thereby splitting the error between the end points. For example, if the TVG range is set to operate between 20 and 60 dB, the DC offset correction is set to compensate for the error at 40 dB. The problem with this technique is that it introduces errors to echo amplitudes that are undesirable for an accurate flaw detection and sizing.

(d) Logarithmic amplifiers are used to cover the huge dynamic range required and the echoes are shown on the waveform display 18 on a logarithmic scale. The logarithmic scale provides a very high dynamic range thereby allowing both a low amplitude flaw echo and the peak of the much higher amplitude back wall echo to be visible on a waveform display.

Unfortunately, certain undesirable consequences occur when using the logarithmic method. Thus, for a given back wall echo amplitude and amplitude variation, the vertical variation of the peak of the echo waveform is much less noticeable on the waveform display than for a receiver that uses linear amplifiers. This would make it more difficult to detect a flaw by observing the peak amplitude variation of the back wall echo, as described earlier.

Further, the output of the logarithmic amplifier can only provide a rectified waveform. Therefore, the location of the negative echo lobe cannot be identified because it is either removed by half-wave rectification, or converted into a positive lobe by full wave rectification. The precise location of both the positive and negative echo lobes is very important for measuring the thickness of target object 14 accurately because one lobe may be more visible than the other. The polarity of the echo lobes is also required to determine when echo phase inversion occurs. Phase inversion of an ultrasonic echo occurs when a sound wave passes from a material of low acoustic impedance to a material of high acoustic impedance.

Furthermore, all filters must be located prior to the logarithmic amplifier section because the filters require linear signals to operate correctly (a logarithmic amplifier is a non-linear device). The receiver will have a much higher susceptibility to noise if the filter circuits are located prior to the high gain logarithmic amplifier section because the PCB traces required to connect the filter components together are susceptible to electromagnetic noise, and the internal noise generated by an filter amplifiers will be maximally amplified. These problems with logarithmic amplifiers are ameliorated in the present invention because the full dynamic range of the sampled data is provided on every sample clock cycle, thereby allowing it to be rendered as linear scale or logarithmic scale. Accordingly, the present invention enables an operator to instruct the system, eg the FPGA described further on, to select and develop for display on display 18 either a linear or logarithmic system output or to store such outputs for later analysis.

This present invention aims to ameliorate or avoid the drawbacks of the prior art and, in effect, is essentially equivalent to a 100 MHz 24 bit A/D converter that works with a large input voltage, free of the DC offsets, base line errors and other drawbacks of the prior art. It is important to note that although the invention was implemented with performance essentially equivalent to a 100 MHz 24 bit A/D converter, as described above, it may also be implemented with a sampling frequency and resolution other than 100 MHz and 24 bits respectively. It utilizes three (or more) A/D converters operating in a corresponding number of channels. The instant inventors recognize that the eventual development of multifunction operating A/D converters will permit the use of a lower number of A/D converters.

Figure 6:
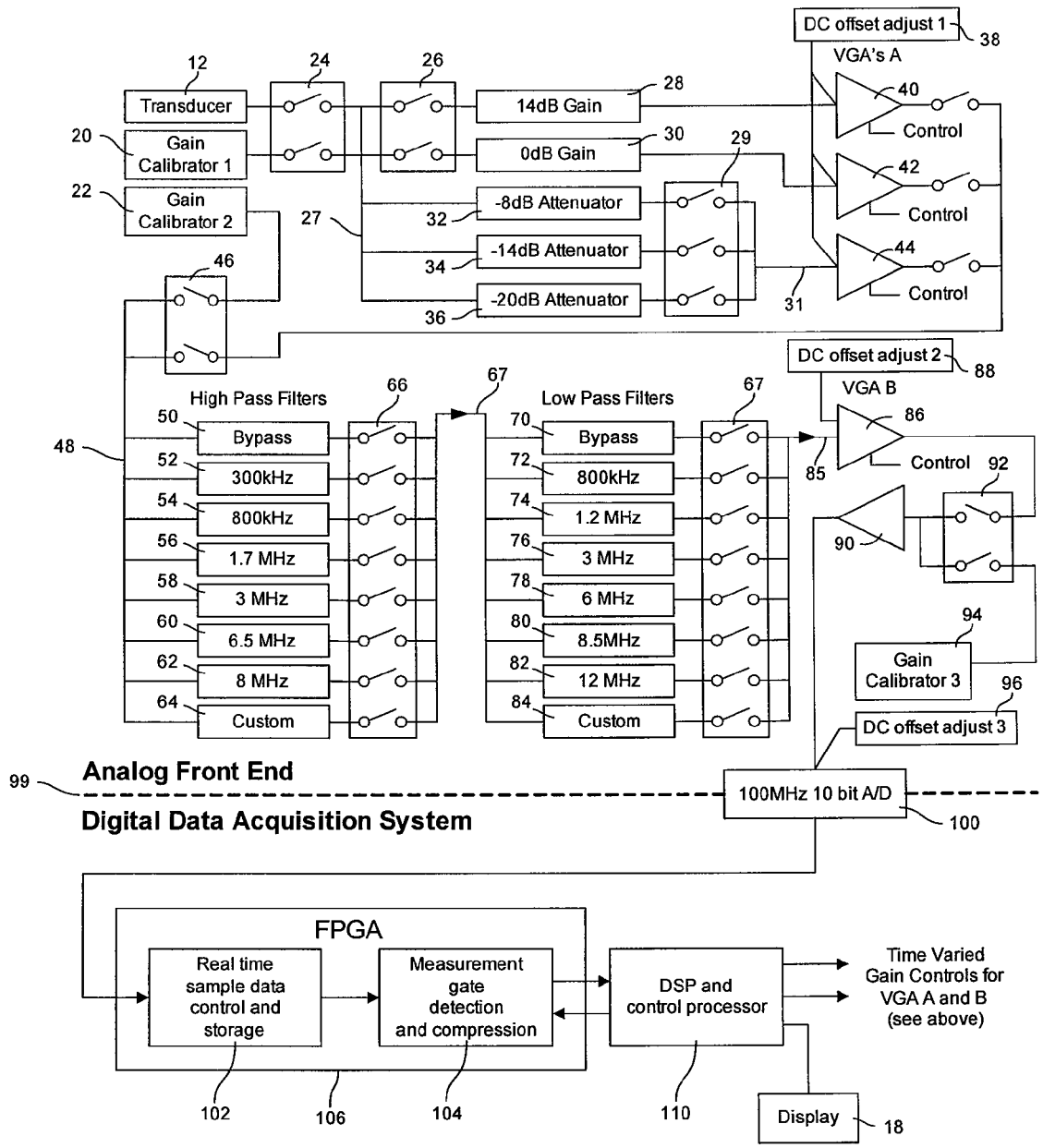
FIG. 6 illustrates a circuit block diagram of a prior art implementation of an ultrasonic inspection apparatus.

A more detailed version of a prior art circuit which has been utilized to implement an ultrasonic inspection system is illustrated in block diagram form in FIG. 6. This intensely analog circuit utilizes the signal from the transducer 12 to feed it through a switch 24 as one selectable input to a series of parallelly provided amplifiers/attenuators 28, 30, 32, 34 and 36, which have respective gains of 14 dB, 0 dB, −8 dB, −14 dB and −20 dB, respectively. The switch 24 also receives the input of a gain calibrator 20 and provides its signal directly to attenuators 32, 34 and 36, and via switch 26 to the amplifiers 28 and 30.

Variable gain amplifiers (VGA) 40, 42 and 44 respectively receive their inputs from the amplifiers 28 and 30 and from the switch 29, which provides an output 31 that constitutes the selected one of the outputs of attenuators 32, 34 and 36. The outputs of the VGAs are provided to a switch 46 which also receives as one of its inputs, a signal from gain calibrator 22 and selectively providing these signals over a bus line 48 to a series of high pass filters 50, 52, 54, 56, 58, 60, 62 and 64, whose outputs are switched through a switching network 66 to low pass filters 70, 72, 74, 76, 78, 80, 82 and 84. Thus, the signals from the VGAs 40, 42 and 44 or from the gain calibrator 22 can be fed by controlling the selection o a desired signal through the switches 66 and 67 to provide it to a further, downstream VGA 86, whose output is further provided through a switch 92 to an amplifier 90.

The output of amplifier 90 or the output of a gain calibrator 94 are then finally fed to the 100 MHz 10 bit analog to digital (A/D) converter 100.

A field programmable gate array (FPGA) 106 incorporates a real time sample data control and storage circuit 102, and a measurement gain detection and compression circuit 104 to provide an output to the digital signal processor and control, which also controls the settings of the FPGA 106 to obtain the appropriately processed output of the analog to digital converter 100, provides time varied gain control, and produces a signal that can be displayed on the display 18.

In view of the introductory discussion, it is readily apparent that the tasks of calibrating the various analog circuits to prevent inconsistencies and variations attributable to different frequency responses of the numerous high pass and low pass filters, and avoiding the DC offsets and drifts and a temperature effects of the analog devices present enormous challenges to both designers and users of the prior art circuits.

Figure 7:
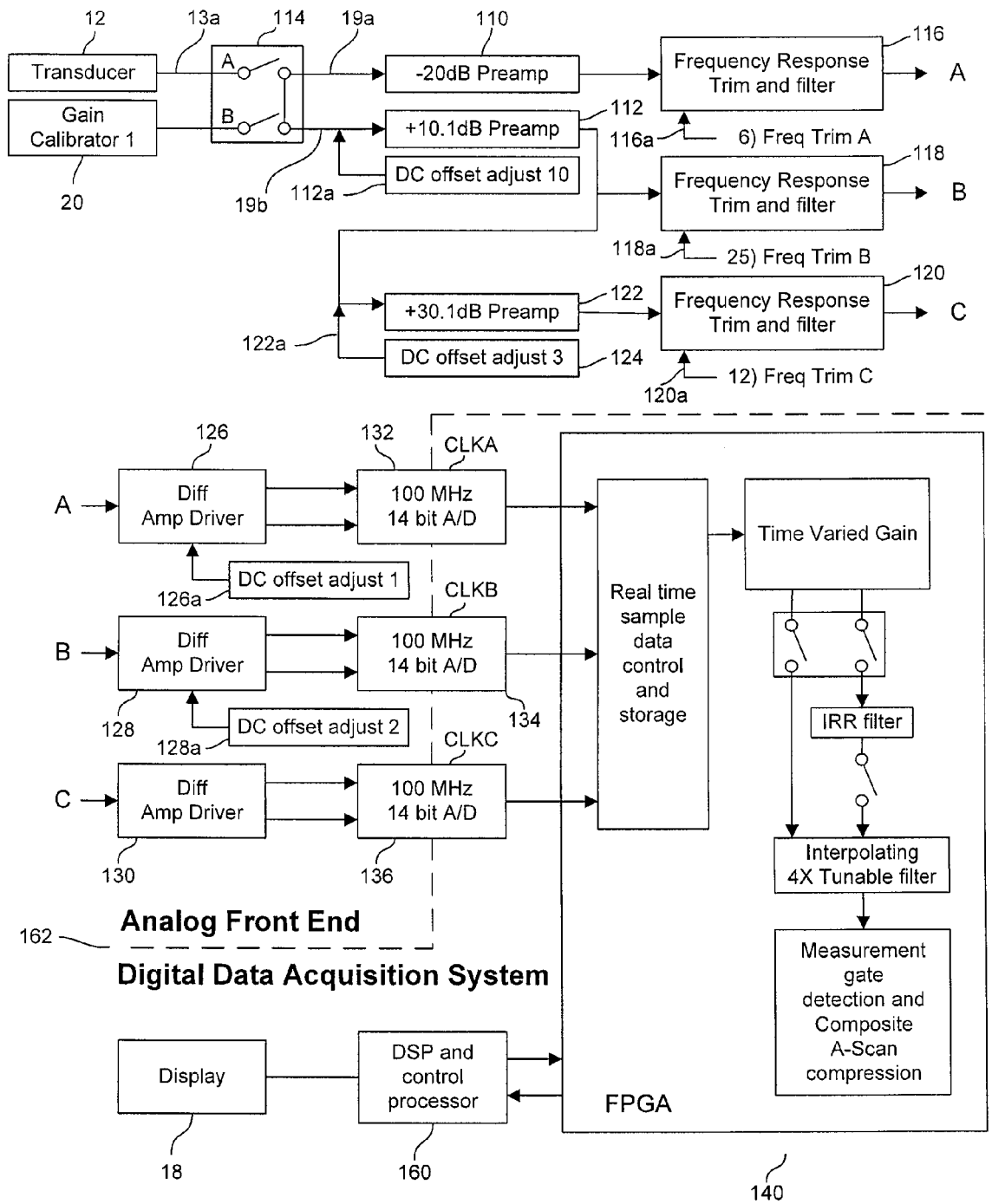
FIG. 7 is a circuit diagram of a digitally intensive implementation of an ultrasonic inspection apparatus in accordance with the present invention.

A cursory comparison of the block diagram of the present invention presented in FIG. 7 illustrates the far scarcer usage of the problem prone analog circuits in the instant invention, which utilize triple A/D channels that avoid many of the drawbacks and complexities of the prior art.

In the block diagram of FIG. 7, when switch 114a is closed the transducer 12 has its output 13a provided directly to only two preamplifiers 110 and 112, the latter amplifier feeding a third amplifier 122. The signals of these amplifiers are processed, respectively, in frequency response trim and filter blocks 116, 118 and 120 and subsequently provided along the three channels A, B, C to differential amplifier drivers 126, 128 and 130. The analog signals along the three channels are then provided directly to A/D converters 132, 134 and 136, respectively, whose digital outputs in turn are then supplied to the field programmable gate array 140, which incorporates control and storage block 142, time varied gain, and measurement gate detection and composite A-scan compression circuit 152. This FPGA 140 works in conjunction with the DSP 160, which provides its signal to the display 18.

The implementation in FIG. 7 (the functionality and features of which are discussed in greater detail below in relation to the description of FIGS. 8a and 8b) dispenses with most of the analog circuits and the drawbacks of the prior art, including the intensive use of analog high pass and low pass filters, additional amplifiers and calibrators, and various VGA circuits, all of which are rendered unnecessary in accordance with the circuits of FIGS. 7, 8a and 8b.

Figure 8A:
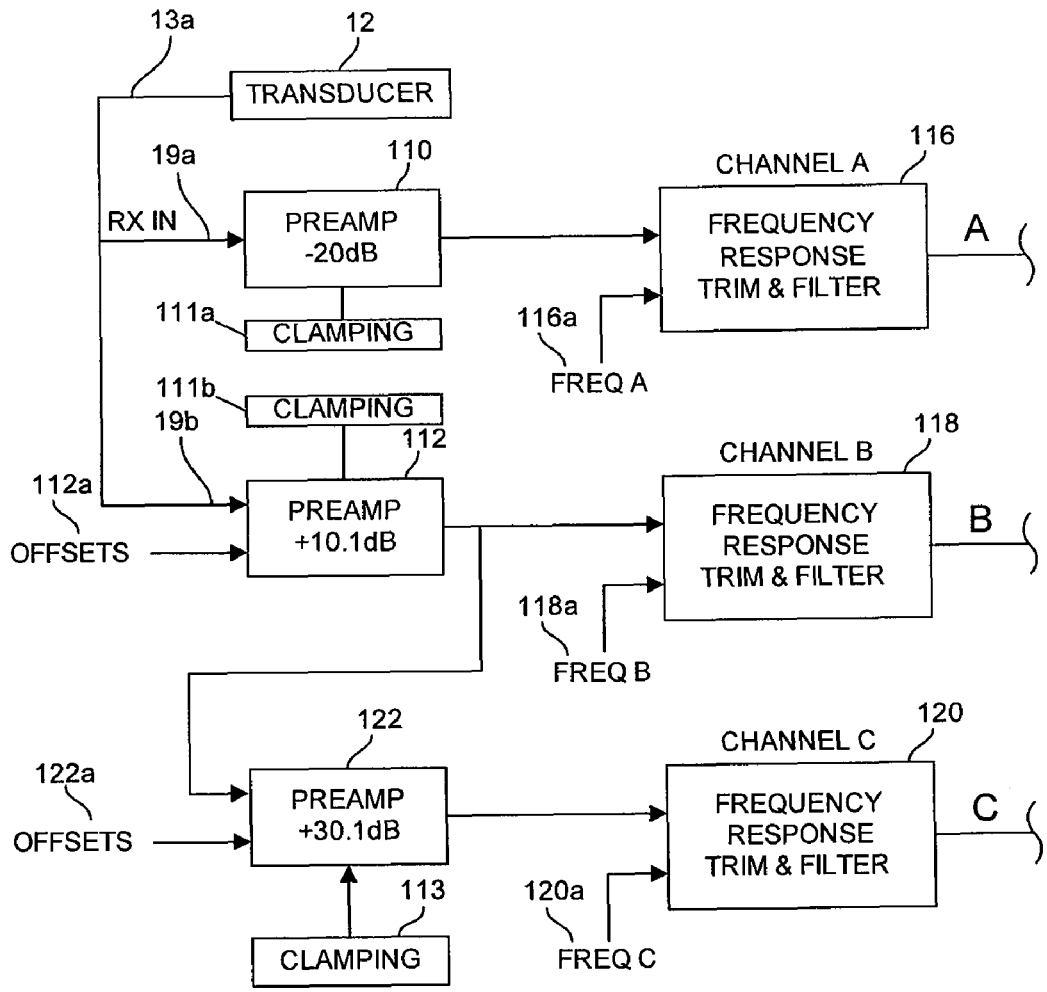
FIGS. 8a and 8b are further block diagrams of a further implementation of the present invention.
Figure 8B:
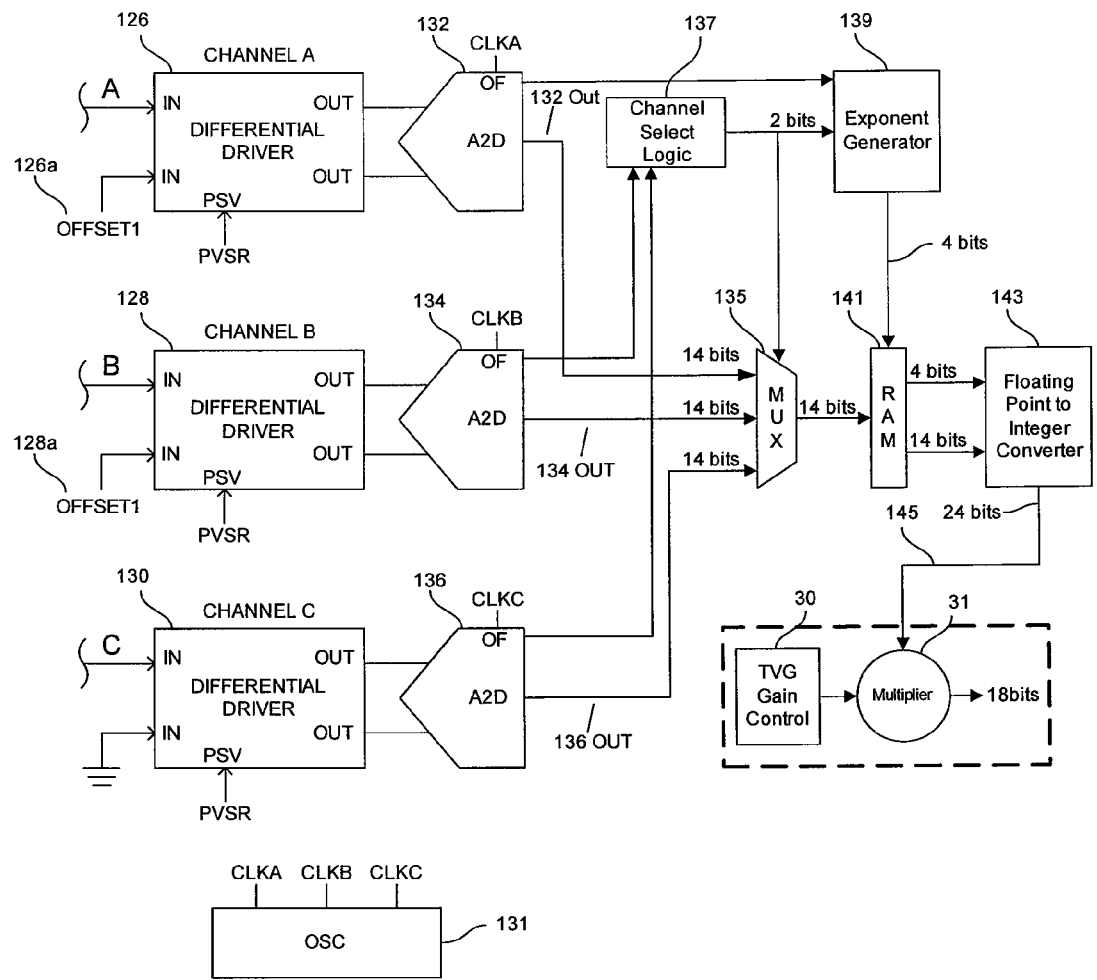

Thus, as further shown in FIGS. 8a and 8b, the present invention is an apparatus and method for extending the dynamic range of an A/D converter circuit used in a flaw detector, thickness or corrosion measurement instrument that eliminates the need for a Variable Gain Amplifier (VGA) circuit and its associated complexity and performance limitations. The apparatus and method of the invention utilize three A/D converters that sample on different channels three differently scaled versions of the same input signal. The sample times of each channel are adjusted to compensate for the propagation delays of each preamplifier channel to minimize signal skew errors between the sample data output of each A/D converter. The scaling is such that the maximum gain channel (C) has a resolution that is 32 times higher than the mid-gain channel (B), and 1024 times higher than the minimum gain channel (A). The higher resolution channels are monitored for data overflow, and the channel that has the highest resolution data without overflow is selected as the output. The selected outputs are merged to produce a seamless stream of output data. The resultant output is a stream of data in which the quantization step-size is larger for large signals and 32 or 1024 times smaller for small signals. The level of dynamic range thus provided by the present invention eliminates the implementation of the traditional VGA to control the level of the analog input signal to keep the peak voltage level of the analog input signal at or near the full-scale value of the input for the A/D converter.

When sampled with the circuit of FIGS. 8a and 8b, the input signal from the transducer 12 is split into two channels 19a and 19b, with respective buffers dedicated for each respective channel. Thus, respective preamplifiers 110 and 112 amplify the input signal 13a on respective channels with a gain of 0.1 (−20 dB) and a gain of 3.2 (10.1 db), respectively. The output of preamplifier 112 is connected to the input of preamplifier 122 to create the third channel which has a gain of 102.4 (40.2 dB). Each channel is sampled by one of three substantially identical A/D converters 132, 134, 136. The three channels A, B, C are sampled with time delays between them to compensate for input signal timing skew errors caused by the propagation delays of all of the amplifiers in the analog signal path. The time delays are controlled by the rising edges of the clocks CLKA, CLKB, CLKC that drive the A/D converters, which clocks are adjusted by a calibration algorithm.

In embodiments that have been reduced to practice, sample timing adjustment is separated into two parts.

A) Course adjustment: using one FIFO and control circuit for each A/D channel, data is delayed by a selectable integer number of clock cycles.

B) Fine adjustment: There are four Phase locked loops (PLL) running 0, 90, 180 and 270 phase angles relative to the clock. By independently selecting a PLL output for each A/D, the clock timing of each A/D can be adjusted in steps of ¼ of a clock cycle.

If the converted data of the maximum gain channel (C) is valid, then its result is passed through unmodified as output 132OUT of the three channel A/D converter circuit (FIG. 8b). If the converted data of the maximum gain channel (C) has overflowed, then its result is discarded, and the result of the converted data of the mid-gain channel (B), if it has not overflowed, is passed through, scaled to correct for the gain of preamplifier 112 and used as output 134OUT. If the converted data of the mid-gain channel (B) has overflowed, then its result is discarded as well, and the result of the converted data of the minimum gain channel is scaled to correct for the signal path gain. This scaled gain is calculated as:

Gains of: preamplifier 112+preamplifier 122−preamplifier 110, which is then used as output 136OUT.

In the embodiment illustrated in FIGS. 8a and 8b, the three channel A/D converter circuit of the invention is capable of: eliminating signal offset errors in all three separate channels; scaling the input signal by using three independent preamplifier channels each set to a different gain; converting the analog signal input to each of three separate channels to a digital signal at respective sample times that are adjustable to compensate for input signal timing skew errors; detecting a channel overflow condition at least in channels having higher gains; and merging the A/D converter outputs of the three channels in real time.

As noted above, the analog input signal 13a from the transducer 12 is directed to two signal clamping amplifier channels, characterized by two clamping elements 111a and 111b, where the second amplifier 112 of the two amplifier channels has a gain that is higher than the gain of the first channel 110 by a predetermined factor. The output of the channel B amplifier 112 is connected both to the downstream filter 118 and also to amplifier 122 with a gain of 32 to create channel C. For example, channel A has a gain of 0.1, while channel B has a gain of 3.2, and channel C has a gain of 102.4. Thus, compared to each other, channel A and B differ by a gain factor of 32, channel C and B differ by a gain factor of 32, and channel A and C differ by a gain factor of 1024.

Clamping voltage thresholds for amplifiers 110 and 112 are set to levels such that the resulting output slightly exceeds the valid input range of respective channel A, B and C A/D converters 132, 134 and 136. The clamp circuits 111a, 111b, and 113 also limit the input voltage to the gain channel amplifiers to prevent them from entering into saturation.

The prevention of amplifier saturation is important because once in saturation, it takes a considerable amount of time for an amplifier to return to its linear region of operation. By preventing the amplifiers in the gain channels from becoming saturated, the length of time the higher gain A/D converters are in the overflow condition is minimized, thereby allowing the higher resolution output data to be used sooner. The clamp circuit in preamp 112 also serves to maintain a constant input impedance for input signal 19a, regardless of the input signal level up to a signal level higher than the maximum input to channel A preamp 110. The input signal would become distorted if a constant input impedance was not maintained.

The present inventor recognizes that amplifier 122 does not require clamp 113 to maintain a constant input impedance for transducer 12 over its signal amplitude operating range because amplifier 122 is isolated from transducer 12 by means of amplifier 112. Because of this, another amplifier circuit configuration can be used for amplifier 122 if needed to provide other benefits such as lower power or less circuit complexity.

In an embodiment that has been reduced to practice, the channel C amplifier 122 is allowed to saturate and fast recovery OpAmps are used. Preferably, clamping may be added to generate less noise.

The output of each gain channel amplifier 110, 112, 122 is connected to Frequency Response Trim and Filter circuits 116, 118, 120, respectively. Frequency response adjustment control signals 116a, 118a, 120a, are respectively used to make the frequency response of channels A, B and C match as closely as possible. This is required to make sure that all signal frequencies of interest have as close to the same gain as possible. A calibration algorithm is used to adjust the frequency response as described above. This frequency trimming method may be used for two or more analog to digital converter channels.

The anti-aliasing filter function for channels A, B and C is distributed within Frequency Response Trim & Filters 116, 118 and 120 and Differential Amplifiers 126, 128 and 130 respectively.

The DC offsets inherent in the amplifiers of each channel are compensated for by injecting DC signals 112a, 122a, 126a and 128a to counterbalance the DC offset errors present throughout the analog signal path. A calibration algorithm is used to perform this compensation. It should be noted that this DC offset compensation method has the following two limitations:

1) At very fast pulser/receiver repetition rates (To of FIG. 2), there is not sufficient time available between To cycles to perform the DC offset correction process required to compensate for DC offset drift over time. This limits the DC offset calibration to only occur when the instrument is not measuring.
2) At very high gain settings, the small DC offset error that remains after counterbalancing will produce a significant offset in the stored sample data, and subsequently in the waveform that appears on the display.

Figure 8C:
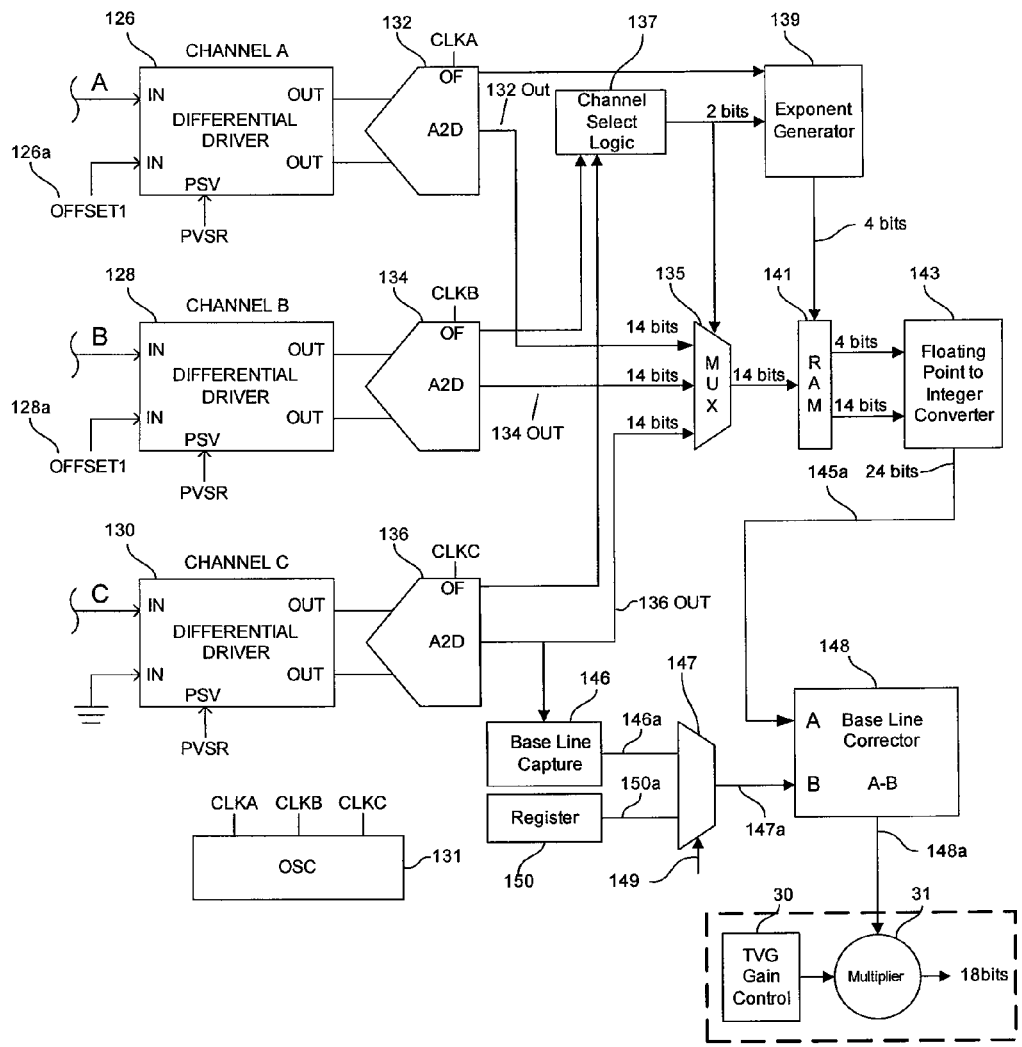
FIG. 8c corresponds to FIG. 8b, but includes purely digital DC offset compensation.

To further ameliorate the effects of DC offset errors present throughout the analog signal path, including the effects described in items 1 and 2 above, the present embodiment includes the purely digital DC offset compensation method, a block diagram of which is shown FIG. 8c.

Figure 3:
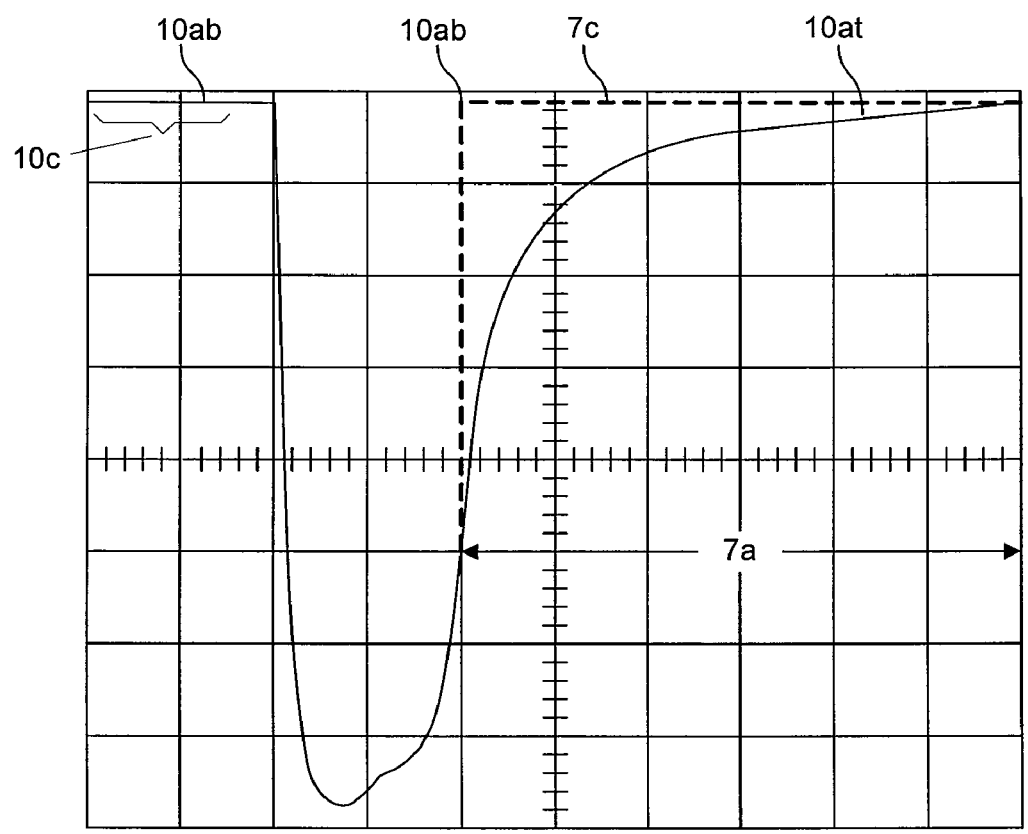
FIG. 3 is a waveform diagram illustrating the trailing edge characteristic of an ultrasonic pulse.

With further reference to FIG. 8c, the output of A/D converter 136 is provided to Base Line Capture block 146 during the interval 10c shown in FIG. 3. Sample points from interval 10c are used to monitor the base line because they are in a relatively 'quiet' region in time—i.e. a region that occurs before the pulser fires and after ultrasonic response signals of substantial amplitude will be present. In the present embodiment, Base Line Capture block 146 uses 256 signed integer sample points and calculates the average; however, a different number of sample points may be used. When multiplexer 147 is enabled by control signal 149 to allow the signed integer output of Base Line Capture block 146 to pass through to Base Line Corrector block 148, signal 147a is subtracted from signed integer signal 145a to remove the base line error. Register 150 is intended to allow alternate base line compensation value to be used that may have been produced by a software algorithm or hardware device not shown.

The A/D converters 132, 134 and 136 of the three channels are 14 bit, high speed converters for which sample timing is provided by the sample clocks CLKA, CLKB, CLKC derived from a 100 MHz oscillator block 131 using respective delay control elements contained within a FPGA circuit. The delay control elements enable adjusting the placement of the rising edges of the sample clock of one channel in time with respect to a clock circuit portion of another channel so that the sample times of each channel are adjusted to compensate for the propagation delays of each preamplifier channel and any other source of timing skew revealed by examination of the A/D converter output data. A calibration algorithm is used to perform this compensation.

As previously noted, in embodiments that have been reduced to practice, sample timing adjustment is separated into two parts.

1) Course adjustment: using one FIFO and control circuit for each A/D channel, data is delayed by a selectable integer number of clock cycles.
2) Fine adjustment: There are four Phase locked loops (PLL) running 0, 90, 180 and 270 phase angles relative to the clock. By independently selecting a PLL output for each A/D, the clock timing of each A/D can be adjusted in steps of ¼ of a clock cycle.

The present inventor contemplates an alternate method of adjusting the sample data timing by use of a fine analog adjustment in conjunction with the course digital adjustment described above. An adjustable signal delay element would be used to adjust the timing of the analog signals instead of the digital clock timing adjustment method described above. This analog signal delay could be accomplished by using any one of the following methods.

1) A delay line with taps, a tap is selected by a switch to adjust the delay.
2) Delay filter elements switched in or out of the signal path as needed.
3) An adjustable delay constructed using a variable element such as an all pass delay filter using a voltage controlled component. The delay could be controlled by a DAC to provide very fine control. The present inventor perceives this method to provide the best adjustment resolution.

A method is also provided to calibrate the system gain by adjusting the full scale range of A/D converters 132, 134 and 136. This is accomplished by adjusting the reference voltage (not shown) of the respective A/D converters using D/A converters (not shown). A calibration algorithm is used to perform this function.

The digital outputs of the A/D converters 132, 134 and 136 are connected to digital multiplexing circuit 135. The overflow signals for the two higher gain A/D converters 134 and 136 are connected to Channel Select Logic circuit 137. Channel Select Logic circuit 137 also extends the time duration of overflow signals from A/D converters 134 and 136 in order to provide time for all of the amplifier circuitry prior to the input of A/D converters 134 and 136 to come out of saturation. This circuit 137 selects the output data bus from the highest gain channel A/D converter that has not overflowed. If all three A/D converter channels are overflowed, the output data bus of the lowest gain channel A/D converter is selected because it will be the first channel to come out of the overflow condition. Channel Select Logic circuit 137 and the overflow signal from A/D converter 132 are connected to an Exponent Generator circuit 139. This circuit 139 calculates the exponent to go with the selected A/D converter data in RAM 141. A floating point conversion circuit 143 effectively adds bits of precision to the A/D conversion for small signals, while maintaining the range capacity for large signals. The floating point converter 143 also reduces the number of bits the sample data RAM requires. The sample data RAM has 18 bits of which 14 bits are used for the mantissa, and 4 bits are used for the exponent. When a sampled value is stored, the selected A/D converter value is stored in the mantissa and an exponent value of 0, 5, or 10 is stored in the exponent to indicate the scale of the data. The exponent may also be set to 15 to indicate that all channels are in the overflow condition. Furthermore, when the data is read from the sample RAM 141, the exponent is used to position the data in the mantissa to construct a 24 bit integer output of the Floating Point to Integer Converter 143. This is the final output 145 of the present invention. This output can be represented by the following formula:

Output 145=$2^{exponent}$×mantissa=24 bit integer

Although the present invention has been described in relation to an embodiment which utilizes three signal processing channels, each incorporating its respective analog to digital converter, the instant inventor also contemplates the use of a lesser number of analog to digital converters or even a single analog to digital converter. Thus, for example, if an analog to digital converter operating at 200 MHz becomes available, two of the channels may be handled by a single analog to digital converter that produces two successive rapid samples of the same signal point. To do so, a first sample of a signal may be taken, while an amplified version of the same signal is delayed (by an analog delay time) for a time delay approximately equal to the clock period of the 200 MHz analog to digital converter. Then the Delayed amplified signal is sampled by the same A/D converter. Also, analog comparators may be utilized to compare the signal magnitudes at the outputs of the preamplifiers to determine their magnitude ranges and to control channeling the signal to that one of the analog to digital converters which will not overflow in response to that signal magnitude.

Further, while three channels have been utilized, it is within the concept of the invention to utilize four or more channels for the purpose of increasing the overall dynamic range of the testing system and/or for a purpose of using a given analog to digital converter as a temporary substitute for any one of the analog to digital converters which has temporarily overflowed by having been saturated.

Elaborating on the aforementioned extensions of the present invention, one implementation may be in the form of a two channel system using a pair of 16 bit ultra fast analog to digital converters, the clock speeds of which are sufficient for applications of the present invention. Note further, that the full dynamic range is not always required in every application, as specific users may require less than a full dynamic range and so may be able to use only one of the multiple analog to digital converter channels. In a two channel system, with one of the channels switched between low gain and high gain, it would be possible to provide a good portion of the benefits of a three channel system, utilizing only two channels.

Relative to the aforementioned problem of detecting flaw echoes that are very close to the back wall of the target object, the present inventor recognizes that the problem can be solved if both channels are stored and the channel change is carried out in the post processing. This would be a 'tracking back wall attenuator' solution. Also a dual or split display window could be used, one to show flaws and the other the back wall. This would remove the need to track the back wall and adjust the display. A small section of the received signal would be displayed twice—once at high gain in the flaw section and then again at low gain in the back wall section. This method can only support a flaw alarm gate that detects flaws that are very close to the back wall if the gate position is calculated in the post processing.

Relative to the aforementioned concept of adjusting the frequency response of the channels individually to make the assembled data stream fit together without steps or jumps, it should be noted that this can be done using a factory adjustment or a run time adjustment. Note further, that in a three channel system, it may be sufficient to provide the frequency response trims on only two of the channels.

The invention can also be implemented by extending the duration of the over range indication signal to prevent output data of an analog to digital converter from being selected prior to the time when its signal channel has fully recovered from the saturation condition. This can take one or more of the following forms.

1. In a current embodiment, time is added to the end of the over range indicator bit from the analog to digital converter. This feature is implemented within the channel select logic 137, shown in FIG. 8b. It may consist of an OR gate that receives the overflow signal as one input and a shifted version thereof as another input.

2. A digital comparator is used on the channel with the next lower gain to detect when the analog to digital converter is out of severe saturation, even if the analog to digital converter still indicates over range. Adding delay to this "severe saturation" detector is comparable to providing a delay on the over range indicator.

3. The data out of the analog to digital converter is compared to the value of the next lower gain channel to validate the data. The value must be within a prescribed range of the value from the next channel.

4. An analog to digital converter is used that is slow to indicate that it has come out of over range.

It should be noted further that an analog to digital converter may saturate at an input voltage that is higher than over range voltage. This is why providing a delay coming out of saturation is advantageous, whereas a delay coming out of over range is not needed. In the voltage range between over range and saturation, the analog to digital converter may function normally and not need recovery time. In an embodiment that has been reduced to practice, the analog to digital over range indicator has been used as a saturation indicator and will sometimes introduce a delay that is not needed. This unwanted delay is rare and not of any technical significance.

The present inventor also contemplates the use of digital to analog converters to trim the analog to digital converter reference voltages for the effect of trimming the gain. This method is used to extend the range of the user gain control and is different from channel matching.

The present inventor also contemplates the use of a preamp for the mid and high gain channels that does not distort the source signal. This approach is preferable to building or utilizing an amplifier with at least a 20 volt peak output range of very low noise performance. The described approach is also preferable to a hybrid design, where the input uses attenuator steps, but this approach does not have as much dynamic range. Nonetheless, for a low cost market segment, a hybrid design may be preferred.

In the preceding description, reference was made to various technical concerns relating to circuit devices becoming saturated or analog to digital converters indicating over range. Following an initial discussion of the underlying problem, several alternate solutions representing further embodiments of the invention are provided.

Under normal operating conditions, the channel gains for the circuits identified below in brackets are applicable.

Channel A Gain*32≈Channel B Gain   [FIG. 7]

Channel B Gain*32≈Channel C Gain   [FIG. 7]

When a channel is driven into saturation it will be indicated by the overflow output signal of the channel's analog to digital converter, thereby enabling Channel Select Logic 137 to select the best channel to receive the signal. As previously described, the best channel is the one with the highest gain and not in the overflow state. The lowest to the highest gain is Channel A, Channel B and Channel C, respectively. See FIGS. 8b, 8c, 8d, and 8e.

Any, or all, of the above conditions may not be true for very fast slew rate signals, such as the leading edge of the pulser pulse, because the edge is so fast that the amplifiers of all three channels are driven into saturation at substantially the same time.

Due to the slew rate limitations of amplifiers and filters, the analog to digital converters do not saturate immediately, and all three channels move toward saturation at substantially the same rate. If samples are taken from the A/D, while their outputs are slewing to their final values, erroneous readings will be noted. For example, when all three channels are at about ½ full scale (corresponding to an A/D output value (in HEX) of 2FFFC), they will not correspond to the correct input amplitude. The channel readings, none of which indicate an overflow, would be as follows:

Channel A=2FFF, indicating −5V at the input.

Channel B=2FFF, indicating −0.15V at the input.

Channel C=2FFF, indicating −0.005V at the input.

Therefore, the embodiment of FIGS. 8b and 8c will select Channel C because it is the channel with the highest gain and not (yet) in the overflow state. The channel readings above indicate that that Channel A is −5V, or less; therefore, the −0.005V signal (assumed to be at the input of Channel C) would be shown on the display, which would be incorrect.

Figure 8D:
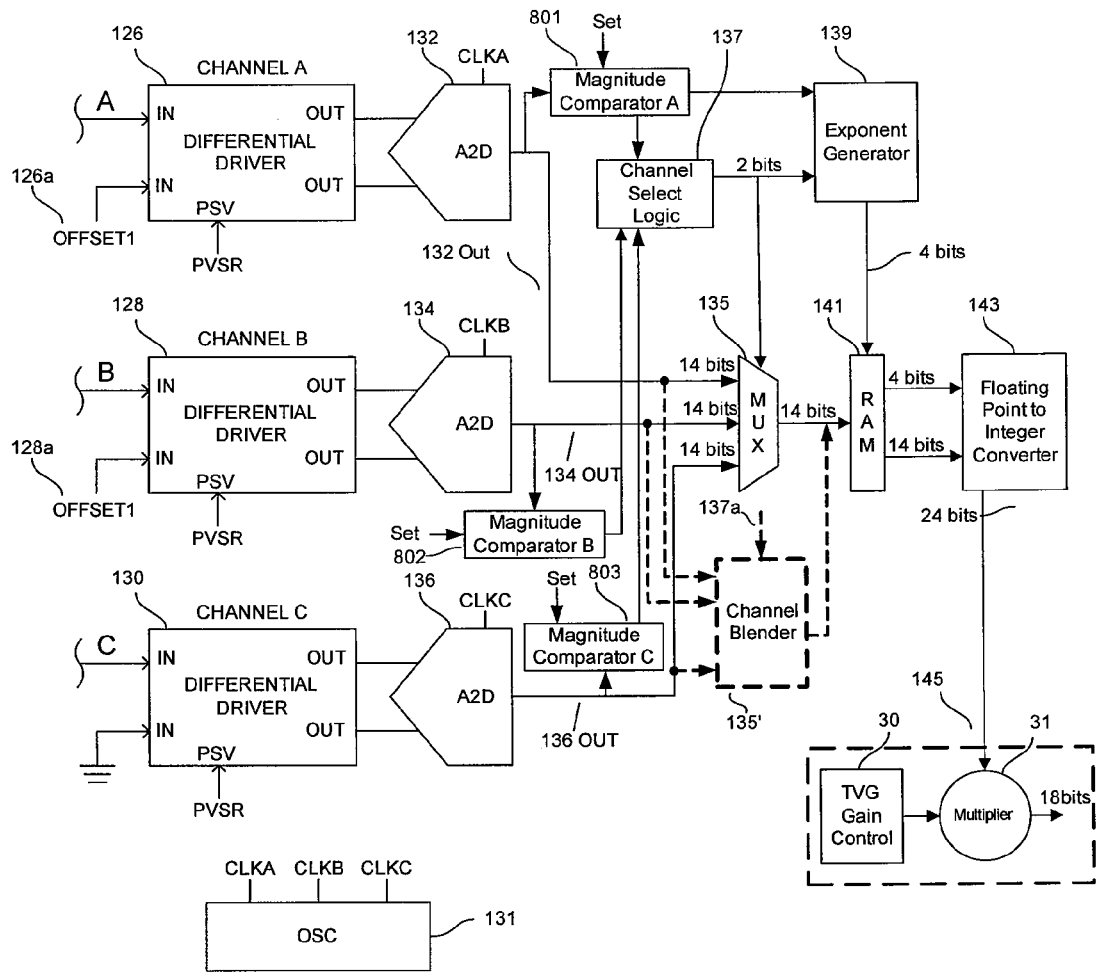
FIGS. 8d and 8e correspond to FIG. 8b, but utilize magnitude comparators instead of overflow indicators, with FIG. 8e adding digital base line correction.
Figure 8E:
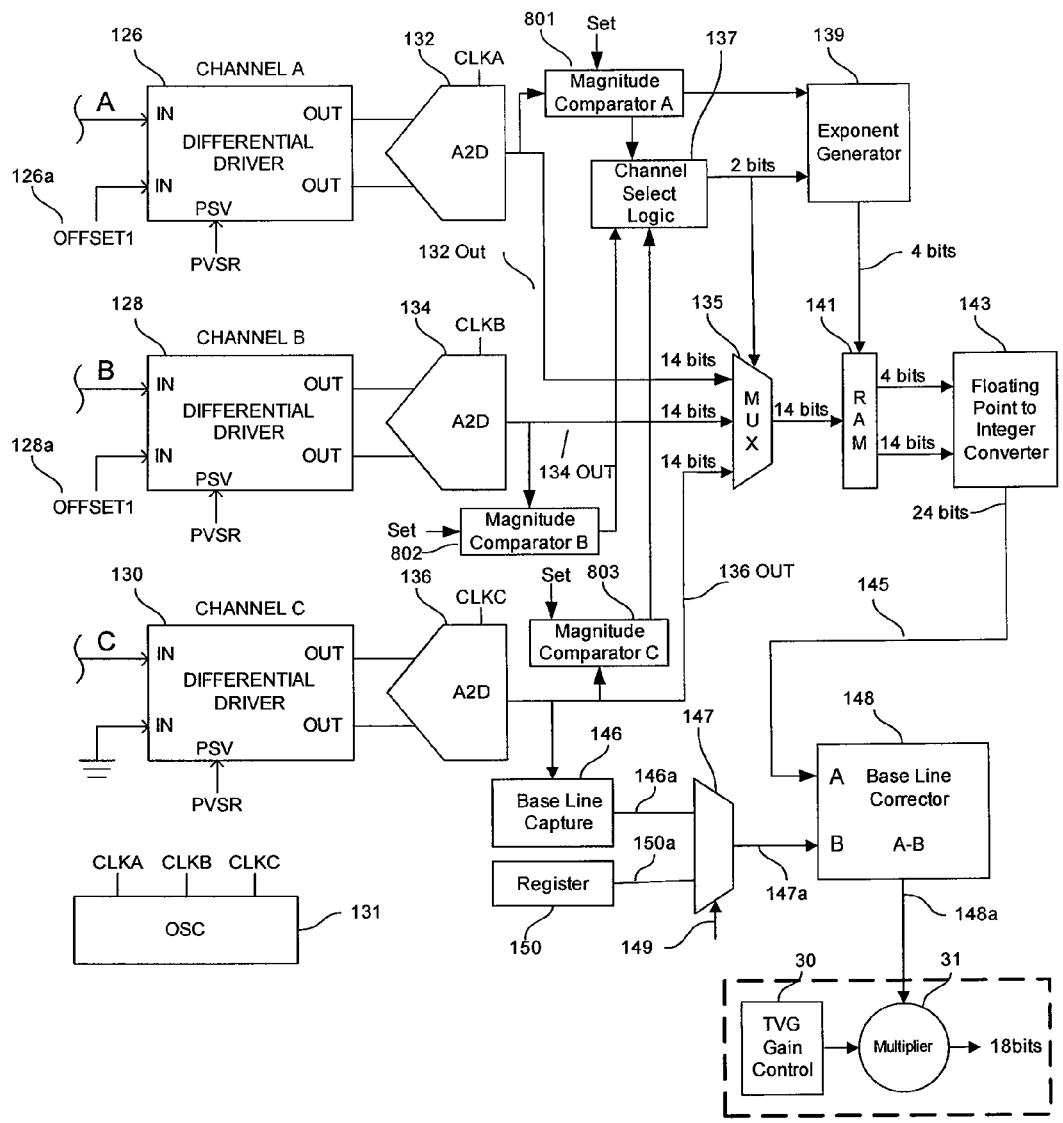

As shown in FIGS. 8d and 8e, an alternate embodiment does not require the use of an overflow output signal from any of analog to digital converters 132, 134 and 136. Instead, magnitude comparators 801, 802 and 803, respectively, are used to indicate when the digital output data of each analog to digital converter matches a predetermined number. Magnitude comparators 801, 802 and 803 provide an output signal to Channel Select Logic 137 when the predetermined number is matched for each. Magnitude comparator 801 also provides its output signal to Exponent Generator 139. It should be noted that the performance of the present embodiment can also be achieved by using only magnitude comparators 801 and 802 for channels A and B, respectively.

Due to the fact that the digital output signal of a channel's analog to digital converter can be correlated to the level of a signal at any point along the input signal path, the primary advantage of the 'magnitude comparator' method is that it can be used to detect any signal level of interest that falls within the full scale of the analog to digital converter and is within its measurement resolution capability. A saturation condition of an amplifier within the input signal path is one example of a signal level of interest.

Figure 10:
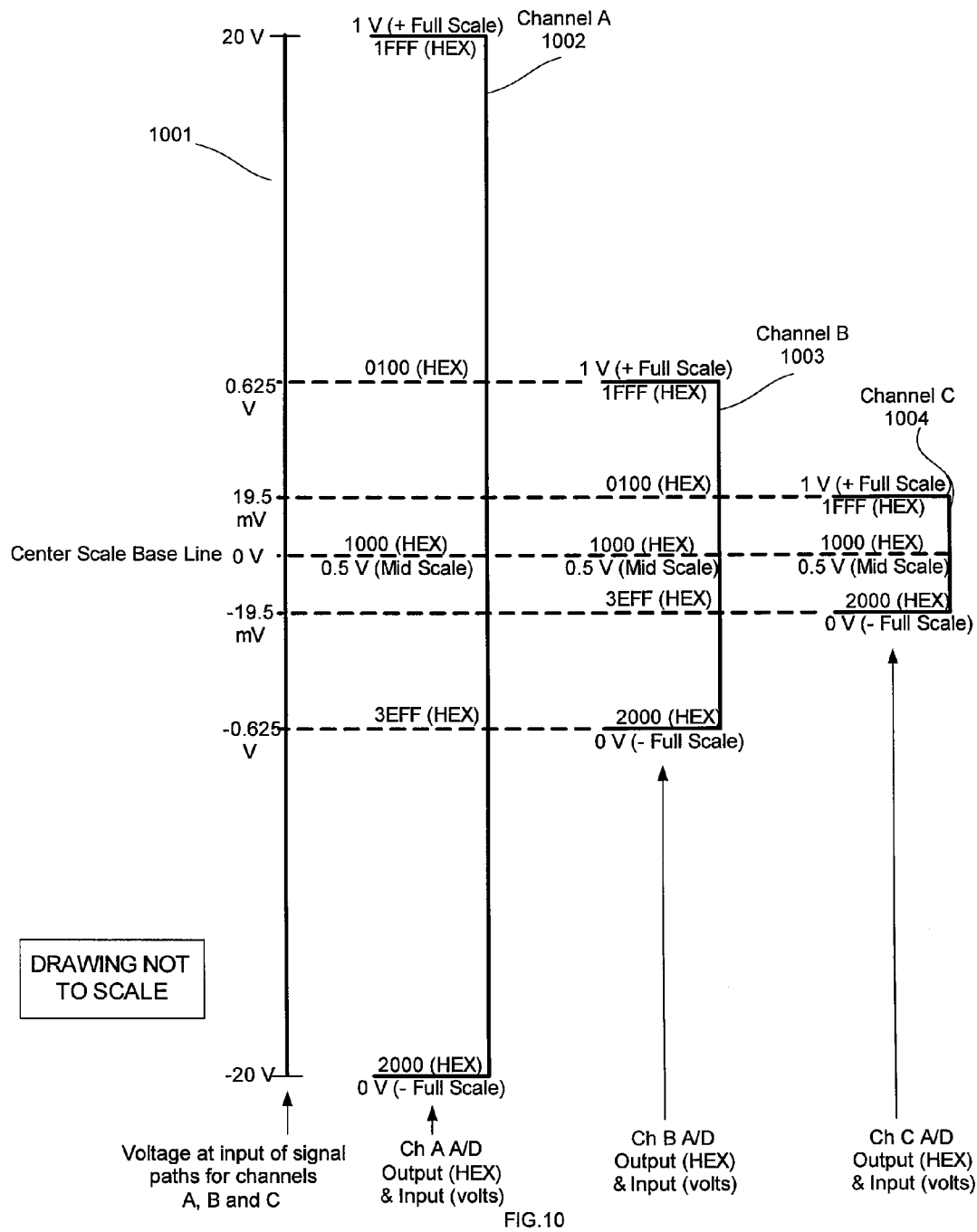
FIG. 10 is a signal diagram utilized to explain certain concepts applicable to the operation of the circuit in FIGS. 8d, 8e and 8h.

Referring to FIG. 10, when processing a very fast signal edge (i.e. fast slew rate) the following logic is true. It should be understood that the values shown below are 14 bit signed integers.

a) IF [Channel A>=100] or [Channel A<=3EFF], then the Channel B and Channel C amplifiers are probably over driven.

b) IF [Channel B>=100] or [Channel B<=3EFF] Then the Channel C amplifier is probably over driven.

Using the logic of a) and b) above, the problem of erroneous channel selection can be prevented by incorporating into Channel Select logic 137 the following rules in the order of priority show below:

a) IF [Channel A>=100] or [Channel A<=3EFF], then use data from Channel A—i.e. Channel A has priority over Channel B b) IF [Channel B>=100] or [Channel B<=3EFF], then use data from Channel B—i.e. Channel B has priority over Channel A c) IF [Channel A<100 and >3EFF] and [Channel B<100 and >3EFF], then use data from Channel C—i.e. Channel C has priority over Channel A and B It should be noted that the hexadecimal values used above and in FIG. 10 were chosen as examples and are not necessarily the values used in an actual embodiment.

FIG. 8d further illustrates in dashed lines a Channel Blender 135' used as an alternative for MUX 135. Channel Blender 135' serves for blending the output of two of the three A/D Converters that have the highest gain, but are not in saturation, in order to minimize the effects of unmatched signals between channels.

Figure 11:
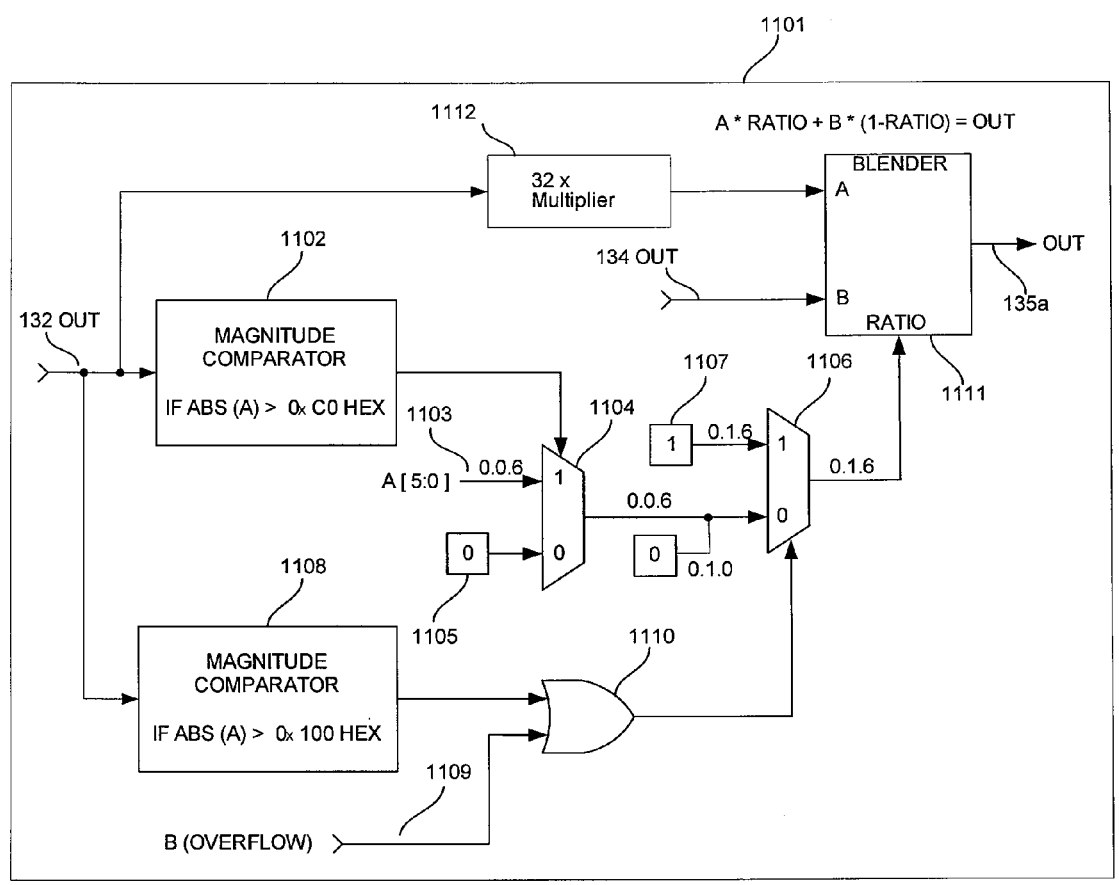
FIG. 11 is a block diagram of a blending circuit associated with FIG. 8d.

FIG. 11 is approximately equivalent to the circuits and signals contained within Channel Blender 135'; however, it only shows the portion for channel A and B, and more output circuits would need to be added to be compatible with the input required for RAM 141.

As used herein, "blending" refers to combining or associating, so that the separate constituents or the line of demarcation is not easily distinguished. Thus, Channel Blender 135' is a device that takes output values from two adjacent A/D converter channels and calculates a compromise value as its output. A ratio control is needed to control the proportions of the two inputs used.

FIG. 11 shows the details of the ratio control circuits.

In this example, the value of the ratio control is limited to the range of 0 to 1.

(Input A)*Ratio+(Input B)*(1−Ratio)=Output

For reasons of circuit simplicity, the ratio control may be further limited to a small set of discrete values that may not include 0 and/or 1. The numbers 0 and 1 produce an output that is identical to one or the other input; some other circuit may handle this condition.

A very simple blender assembled from two adders and three multiplexers could support the following ratio values: 0, 0.25, 0.5, 0.75 and 1. This would divide the channel select anomaly into four separate anomalies, each of one-fourth the magnitude.

Thus, depending on the amplitude of input signal 19a of FIG. 7, Channel Select Logic 137 of FIG. 8d selects the active channel. When this system is used for an application that produces an input signal amplitude very close to a threshold that causes the system to switch channels, it may be observed that, as the system changes channels, a small jump, or glitch, might appear in the output because the gain, frequency response and/or phase of the two channels are not precisely matched. This may manifest itself as an unexpected rise or fall in the output signal amplitude.

Referring to FIG. 8d, the low gain channel is channel A and the high gain channel is channel B. Depending on the outputs of Magnitude Comparators 1102 and 1108 (FIG. 11) contained within Channel Blender 135' (FIG. 8d), Blender 1111 (FIG. 11) measures how close to saturation channel B is. As input signal 19a (FIG. 7) is increased, channel B approaches saturation and the preset value of Magnitude Comparator 1108. When the latter is reached, a blending function is invoked within Channel Blender 135' that mixes the data from A/D converter 134 with data from A/D converter 132. The blend function is variable or has steps of weighting of the two data sources from the respective A/D converters. As channel B approaches saturation the blend-weighting ratio is changed so as to apply more weight to channel A and less to channel B. As an example: starting at a low input signal 19a (FIG. 7) amplitude, the blend ration would be at 100% of channel B and 0% of channel A; as channel B gets closer to saturation, the blend would change to 50% of channel B and 50% of channel A; when channel B is saturated, the blend is 100% of channel A and 0% of channel B. The blend ratio can be extracted from channel A or B or a combination there of. The blend ratio may change in a few steps or adjust smoothly in proportion to the channel signal amplitudes.

The use of Channel Blender 135' makes the input signal 19a (FIG. 7) voltage threshold that separates channel A operation from channel B operation less likely to be observed by the operator. This blend function can be used for all channel transition points. This method can be used in combination with any of the other methods of controlling channel selection.

Figure 8F:
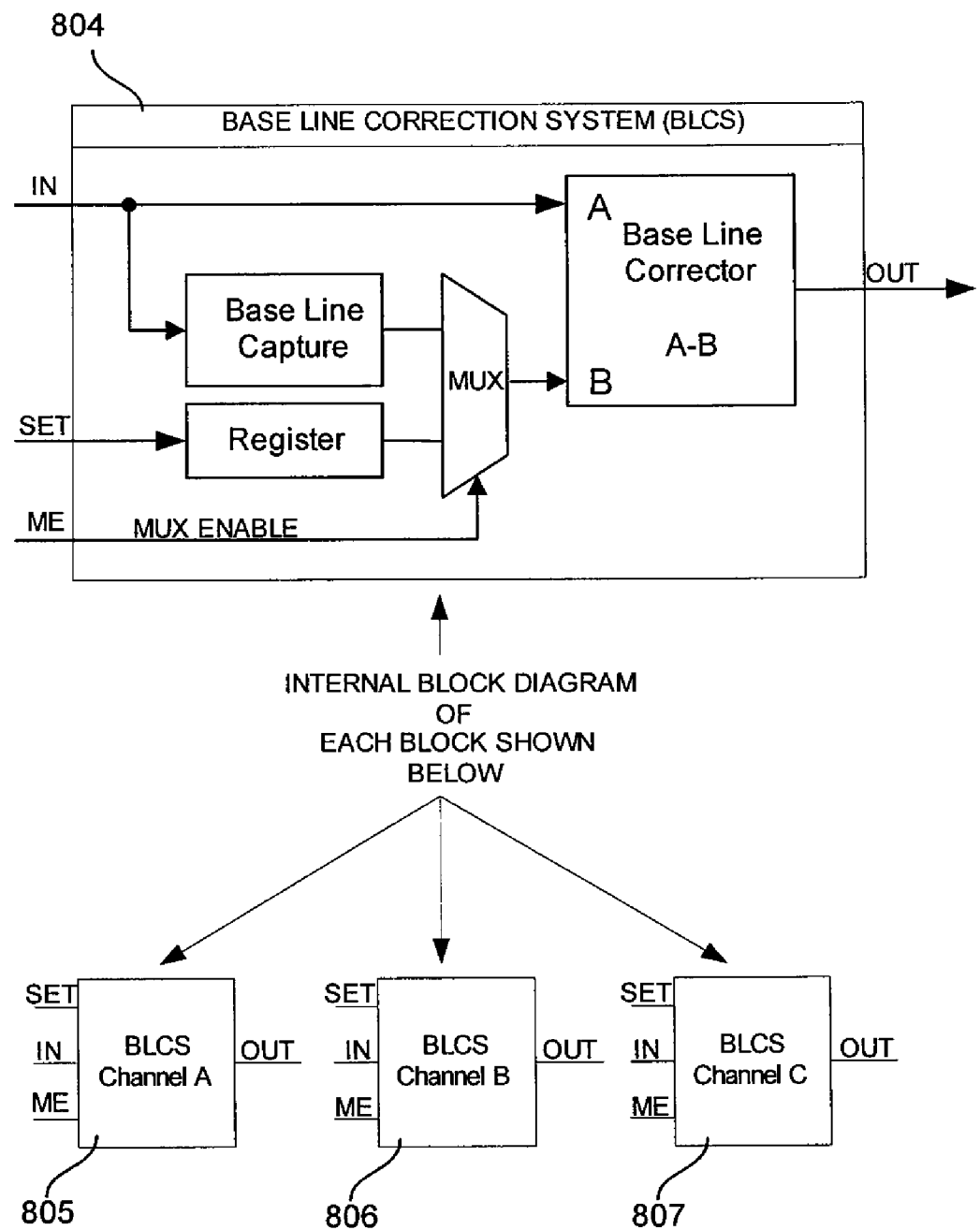
FIGS. 8f and 8g correspond to FIG. 8b, but add base line correction in each channel.
Figure 8G:
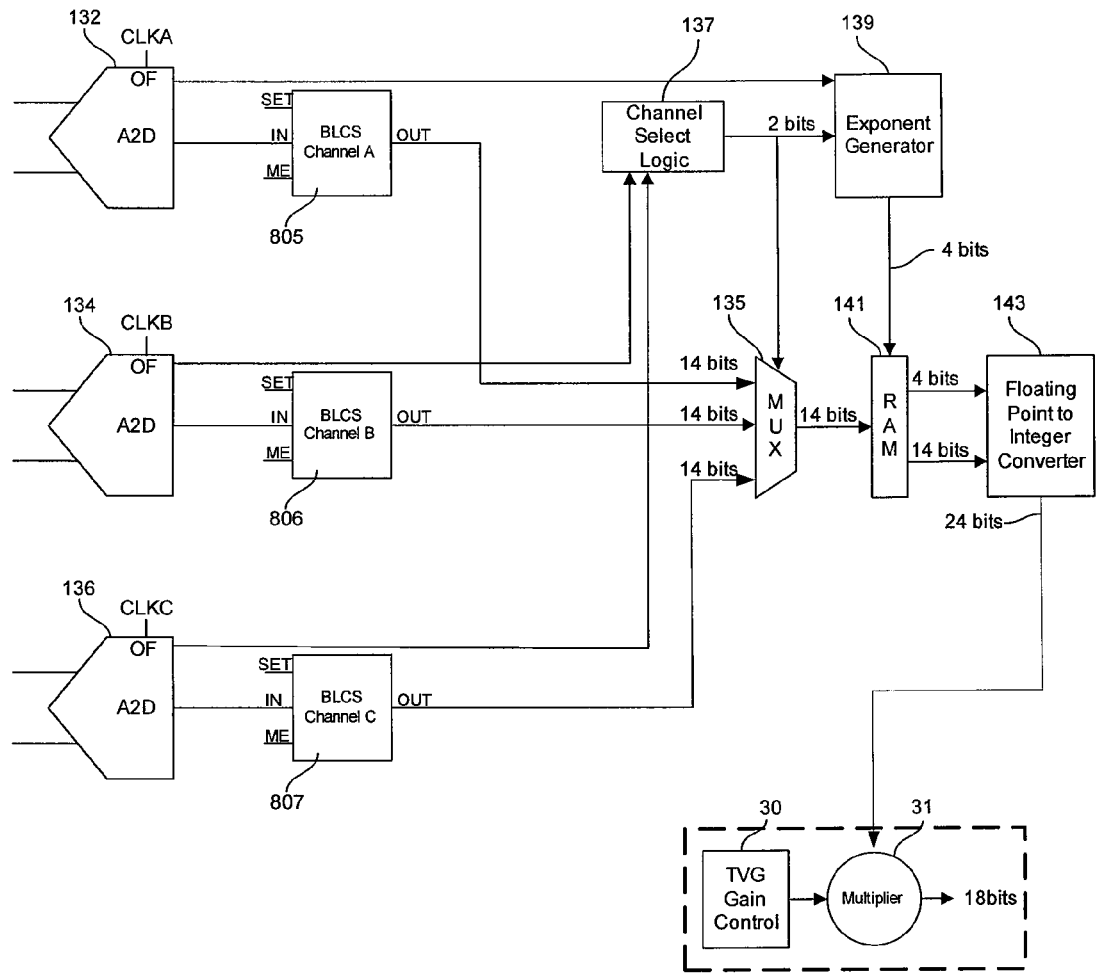
Figure 8H:
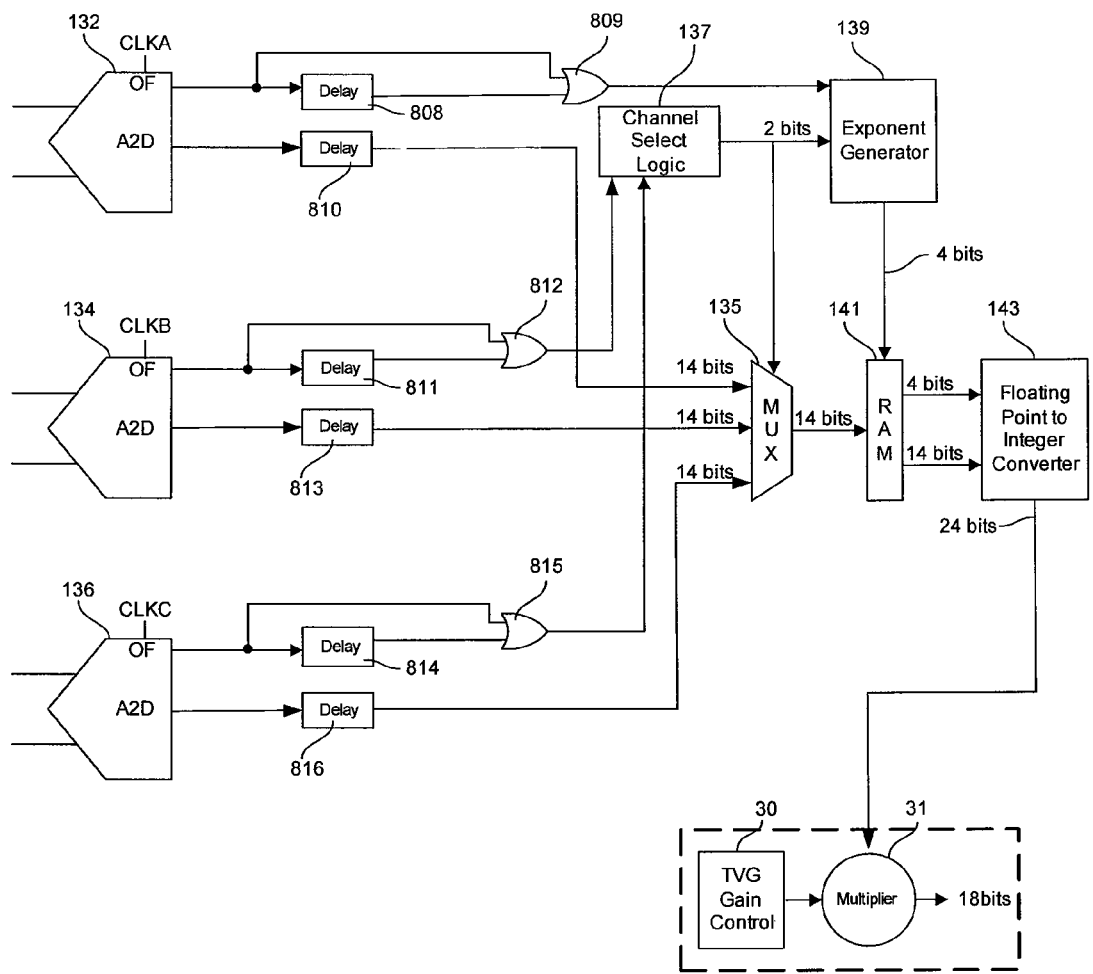
FIG. 8h corresponds to FIG. 8b, but includes delay circuits for dealing with fast slewing input signals.

FIG. 8h provides another solution which adds delay elements 808, 810, 811, 813, 814 and 816 to the output sample data and overflow (OF) signals of analog to digital converters 132, 134 and 136 in order to provide the overflow signals an additional clock cycle to respond before the output sample data is provided to MUX 135. Although not shown, more than one additional clock cycle may be used. The delays prevent Channel Select Logic 137 from selecting a channel until the overflow signals have had sufficient time to respond, thereby preventing the problem caused by a fast slew rate input signals that was described earlier.

In each channel, the overflow and delayed overflow signal are provided to an OR gate in order for the overflow signal to:
a) Turn on without delay so that it will occur prior to the time when the analog to digital converter output sample data is provided to MUX 135, and
b) Turn off with delay in order to be synchronized with the delayed sample data that is provided to the input of MUX 135 upon returning from the overflow state.

It should be noted that delays of other than one clock cycle may also be used for this alternate embodiment.

This method is implemented by inserting a data delay of one sample clock cycle between each digital signal output of analog to digital converters 132, 134 and 136, and the input to MUX 135. A data delay of 1 sample clock is also inserted between the overflow signal of each analog to digital converter and the input to an OR gate. The output of OR gate 809 of channel A is provided to the input of Exponent Generator 139. The output of OR gate 812 and 815 for channel B and C, respectively, are provided to Channel Select Logic 137.

It should be noted that the performance of this alternate embodiment can also be achieved by using delays in channels B and C only.

The present inventor also contemplates a method to make the gain of each channel substantially meet predetermined levels by using only a variable gain mechanism, such as a variable gain amplifier, within in the analog signal path of each channel. The gain levels would be set to predetermined levels by a calibration procedure. The predetermined levels contemplated for the present embodiment are those levels that ensure that the gain scaling between channels A, B and C is as accurate as possible. There are no figures associated with this alternate embodiment.

In the preceding description, reference is made to a base line corrector 148, shown in FIG. 8c. As described below, digital DC offset adjustment can be performed at the output of any of the analog to digital converters, instead of just at the merged output, as shown in FIG. 8c. Accordingly, reference is now made to FIGS. 8e, 8f and 8g, noting the following:
a) Base Line Correction System (BLCS) 804 shown in FIG. 8f is the same as what is shown in FIG. 8e items 146 through 150.
b) Base Line Correction Systems (BLCS) 805, 806 and 807 for channels A, B and C, respectively have the same contents as BLCS 804. BLCS 805, 806 and 807 are redrawn versions of BLCS 804 and are intended to improve the appearance of FIG. 8g.
c) As shown in FIG. 8g, BLCS 805, 806 and 807 are inserted between the digital signal outputs of analog to digital converters 132, 134 and 136, and the input to MUX 135.

With further reference to FIG. 8g, the outputs of A/D converters 132, 134 and 136 are provided to BLCS 805, 806 and 807 during the interval 10c shown in FIG. 3. Sample points from interval 10c are used to monitor the base line because they are in a relatively 'quiet' region in time—i.e. a region that occurs before the pulser fires and after ultrasonic response signals of substantial amplitude will be present. In the present embodiment, BLCS 805, 806 and 807 each use 256 sample points and calculates the average; however, a different number of sample points may be used. The multiplexers within BLCS 805, 806 or 807 can be enabled by their respective control signals (ME) to allow the output of each BLCS to be provided to Base Line Corrector block input B, as shown in FIG. 8f. Input B is then subtracted from the output of A/D converters 132, 134 and 136 to remove the base line error. The Registers contained in BLCS 805, 806 and 807 are intended to allow alternate base line compensation value to be used that may have been produced by a software algorithm or hardware device not shown.

Figure 9:
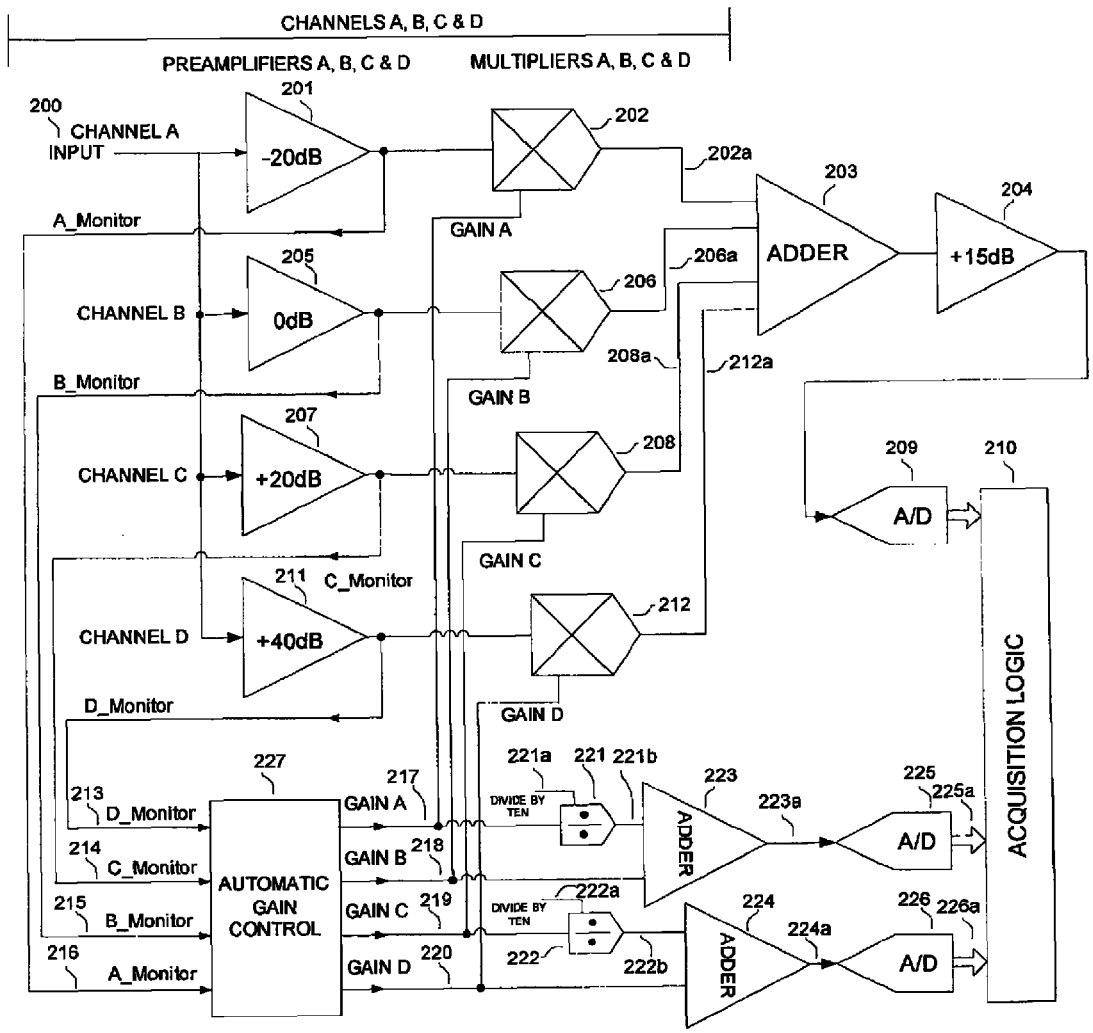
FIG. 9 illustrates a circuit block diagram of an alternate embodiment for the Front End section delineated in FIG. 7.

The present inventor also contemplates an alternate embodiment, as shown in FIG. 9 and described below, that will achieve the benefits of the present invention, especially high dynamic range, by utilizing one signal path A/D Converter in concert with one or more gain reading A/D Converters and an Automatic Gain Control (AGC) circuit to determine and control the gain of the system. Although not shown in FIG. 9, Input signal 10b of FIG. 1 is connected to Input 200 on FIG. 9.

According to one aspect of the alternate embodiment, a data reconstruction device in Acquisition Logic Block 210 is used to compute the system gain and render the appropriate signal amplitude on the display, or provide it as input to another device. Acquisition Logic Block 210 would be located within FPGA 140 of FIG. 7 and the circuitry to the left of it would be replaced substantially by the entirety of FIG. 9. Some of the circuits in FPGA 140 would be modified, or removed, as appropriate per the alternate embodiment.

According to another aspect of the alternate embodiment, the system gain is calculated for every sample point by using the output values of signal A/D Converter 209 in conjunction with the output values of gain reading A/D Converters 225 and 226. The sample rate is substantially the same and synchronous for A/D Converters 209, 225 and 226. The precision of the system gain calculation is substantially determined by the accuracy of the gain calibration system, the transfer characteristics of the multipliers, and the accuracy of the three aforementioned A/D Converters. The present inventor contemplates that calibration for zero multiplication (explained later) and DC offset nulling may be required for each channel.

As can further be seen from FIG. 9, the circuit of the alternate embodiment is comprised of four parallel input gain channels 201, 205, 207, and 211, the output of each provided to one of four gain control Multipliers 202, 206, 208, and 212 respectively, the outputs of which are provided to Adder 203 followed by Amplifier 204, A/D Converter 209, and finally Acquisition Logic 210. AGC circuit 227 receives input from Monitor signals 213, 214, 215 and 216, and provides output gain control signals 217, 218, 219 and 220 to Multipliers 202, 206, 208, and 212 respectively. The present inventor recognizes that that number of channels may be more or less than four depending on the dynamic range required for the application that this alternate embodiment is applied to.

The prevention of the undesirable effects of signal saturation that can occur at different locations along the signal path is a very important aspect of the alternate embodiment. The signal path starts at Input 200 and ends at the input to A/D Converter 209. A saturated signal in the present embodiment is considered any signal in the signal path starting at the output of Preamplifiers 201, 205, 207 and 211 that has an amplitude with an absolute value of greater than 1 volt. The following three conditions can cause saturated signals to be present in the signal path.

1. The absolute value of the amplitude of Input Signal 200 is greater than 10 V peak.
2. The absolute value of the amplitude of Input Signal 200 is less than or equal to 10 volt peak and of sufficient amplitude to cause the output of Preamplifier 205, 207 or 211 to be greater than 1 volt.
3. The absolute value of the amplitude of Input Signal 200 is less than or equal to 10 V peak and the sum of the outputs of Multipliers 202, 206, 208 and 212 at the output of Adder 203 is sufficiently high enough to cause signal saturation at the input of A/D Converter 209.

For condition 1, it is not the object of the alternate embodiment to prevent signal saturation along the signal path because many Flaw Detector inspection procedures require that the pulser signal, which has a peak amplitude absolute value that is much greater than 10 V, to always be present on the display; therefore, the pulser signal must be permitted to saturate the signal path.

For condition 2, a means is provided in the alternate embodiment by use of AGC circuit 227 to substantially prevent the saturated output signals of Preamplifiers 205, 207, and 211 from passing through gain Multipliers 206, 208 and 212 by setting Gain control signals 218, 219 and 220 to substantially zero. The present inventor recognizes that commercially available multiplier components do not possess perfect performance characteristics. Hence, Multipliers 206, 208 and 212 are not required to provide the infinite attenuation associated with a theoretical zero multiplication. Multipliers 206, 208 and 212 are only required to provide sufficient attenuation to keep the maximum peak amplitude of the saturated signal below the level that would cause an undesirable effect to the input signal to A/D Converter 209. The maximum permissible saturated signal level could be established, for example, from a recognized industry standard for Flaw Detector instruments such as the EN12668-1:2000. It is worth noting that the outputs of Multipliers 206, 208 and 212 are summed; therefore calculation of the maximum permissible saturated signal level must take this into account.

For condition 3, a means is provided in the alternate embodiment by use of AGC circuit 227 to ensure that the outputs of Multipliers 202, 206, 208, and 212 are of sufficiently low amplitude to prevent a signal of greater than 1V to occur at the input to A/D Converter 209 after the outputs have been summed by Adder 203 and amplified by +15 db amplifier 204.

According to another aspect of the alternate embodiment, channels A, B, C and D must have substantially equivalent propagation delays and frequency responses up to, and including, the input of Adder 203 to prevent distortion at the summed output.

According to another aspect of the alternate embodiment, the gain of each channel is controlled by multiplier multiplicand signals Gain A, Gain B, Gain C and Gain D which are shown on FIG. 9 as items 217, 218, 219 and 220 respectively. Automatic Gain Control circuit 227 monitors the output of each gain amplifier by means of Monitor signals 216, 215, 214 and 213, and adjusts the gain accordingly. The gain of Multipliers 202, 206, 208 and 212 are controlled in a manner to provide a smooth transition from one multiplier to another thereby preventing abrupt gain changes that can cause signal distortion or glitches.

According to another aspect of the alternate embodiment, Preamplifier 205, 207 or 211, if saturated, is prevented from distorting Input signal 200 by use of the clamping circuit previously described for the invention of FIG. 7. Each clamping circuit prevents distortion of input signal 200 by maintaining a constant input impedance for Preamplifiers 205, 207 and 211.

According to another aspect of the alternate embodiment, A/D Converters 225 and 226 sample the summed Gain signals that are provided to it by Adders 223 and 224 respectively. Gain signals 217 and 219 are each divided by ten in order to scale them to match the sensitivity of Gain signals 218 and 220.

According to another aspect of the alternate embodiment, when the signal amplitude of Input 200 is near zero, the amplitudes of Gain Monitor signals 213, 214, 215 and 216 will also be near zero, thereby causing Automatic Gain Control circuit 227 to turn up Gain signals 217, 218, 219 and 220 to their maximum gain value of 1 volt. As the signal amplitude of Input 200 increases, Multipliers with non-zero gain multiplicands change gradually in order to provide a smooth gain transition between channels prior to reaching a saturation condition. When the amplitude of Input 200 causes D_Monitor signal 213 to reach a predetermined amplitude just below saturation, Automatic Gain Control circuit 227 reduces Gain D 220 to zero to prevent the saturated signal, when it occurs, from passing through Channel D multiplier 212 and causing a substantially saturated signal. When Gain D is set to zero, Input 200 will pass through Channel A, B and C until C_Monitor signal 213 reaches a predetermined amplitude just below saturation, thereby causing the Automatic Gain Control process described above for Channel D to start for Channel C. As the signal amplitude of Input 200 continues to increase, this process occurs for Channel B, then Channel A, ultimately preventing substantially saturated signals from passing through Channels B, C and D.

The response time of AGC circuit 227 establishes the maximum acceptable time rate of change of the input signal 200 because the gain adjustment must occur prior to the moment when input signal 200 reaches the amplitude that will cause an impermissible signal to occur. If the alternate embodiment must work with signals that have a time rate of change that is faster than the response time of the AGC circuit 227, a delay circuit is introduced between the output of Preamplifiers 201, 205, 207 and 211 and the input to Multipliers 202, 206, 208 and 212. Monitor signals 216, 215, 214 and 213 are connected to the input of each delay circuit respectively. The delay circuit provides a time delay that is greater than the response time of the AGC circuit 227. The relative propagation delay and frequency response errors between the delay circuits of each channel must be minimal in order to not cause an unacceptable degree of signal distortion.

The present inventor recognizes that the objectives of the alternate embodiment can be achieved with control parameters and sequences for the Automatic Gain Control circuit 227 that are implemented in ways other than described in the embodiment above. Furthermore, the present inventor recognizes that these other embodiments may accomplish substantially the same end result with respect to gain control.

Throughout the specification and claims, reference is made to "echo" signals. As will be appreciated by people of skill in the art, in certain environments or applications, the transmitter and receiver components of the transducer 12 are physically separated, with the receiver being located on an opposite side of the object being tested. Hence, the term "echo" as used herein also pertains and encompasses embodiments where the so-called echo signal passes through the object being tested.

In the preceding description, the invention that has been described exclusively with respect to embodiments wherein flaw detection is carried out with a single transducer element operating exclusively under the echo principle and/or by reference to a transmitter/receiver pair which handle ultrasound waves that pass through a material. However, it should be noted the present invention is equally applicable to flaw detection instruments that use an array of transducer elements, such as an ultrasonic phased array probe. As is the case with a single element ultrasonic transducer, the response signal for each transducer element of the phased array ultrasonic probe used for reception is provided to the input of a receiver channel for conditioning and subsequent digitization by an analog to digital converter. In other words, the reference in the claims to a "transducer"—in the singular—is deemed to pertain to an ultrasonic phased array type of a probe as well. Such arrays of transducers are deemed to be either identical or at least equivalent to a single element transducer. The structure of such ultrasonic phased array devices is described or referenced in U.S. Pat. Nos. 4,497,210 and 6,789,427, the contents of which patents are incorporated herein by reference.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An object inspection system, comprising:
   a transmit and receive section to generate a test signal and to receive a responsive echo signal;
   a transducer that converts the test signal to an ultrasonic signal, applies the ultrasonic signal to a target object to be tested, receives an ultrasonic echo signal and produces the echo signal for the transmit and receive section;
   a signal processing circuit coupled with the transmit and receive section for receiving and processing the echo signal, the signal processing circuit including at least two signal processing channels, each channel scaling the echo signal to a different degree, and each channel having a respective analog to digital converter which outputs a respective digitized signal;
   a selection circuit which selects the digitized signal of the respective analog to digital converter which provides the largest amplification of the echo signal without having overflowed; and
   a first one of said signal processing channels being coupled directly to the echo signal
   and comprising a respective preamplifier and a respective clamping circuit for preventing said preamplifier from becoming saturated, and a second one of said signal processing channels being coupled directly to the echo signal and comprising a respective preamplifier and a respective clamping circuit to prevent saturation of the preamplifier of the second one of said signal processing channels, the clamping circuit of the second signal processing channel being configured to maintain a constant input impedance on the echo signal, at least up to a signal level of said echo signal which equals a maximum input range to the preamplifier of the first one of said signal processing channels.

2. The system of claim 1, including a display for displaying a scan signal produced by the signal processing circuit and representative of the echo signal.

3. The system of claim 1, further comprising in at least one of the signal channels a respective frequency filter.

4. The system of claim 1, in which each of the analog digital converters has a respective clock input, the clock inputs being synchronized with one another with a phase adjustment between activating clock edges thereof to compensate for signal path delays in each channel.

5. The system of claim 1, further comprising an exponent generator for scaling the output of a selected analog to digital converter output and storing the same in a random access memory.

6. The system of claim 3, wherein the respective frequency filter is an anti-aliasing filter.

7. The system of claim 1, including a DC offset circuit which applies a digital DC offset correction at signal location located after said selection circuit.

8. The system of claim 7, wherein the DC offset circuit includes a baseline capture circuit coupled to at least one of the analog to digital converters to produce a correction signal, and including a baseline corrector which is capable of subtracting the correction signal from an output signal derived from one of the analog to digital converters.

9. The system of claim 4, including a FIFO circuit that enables delaying one clock input relative to another by a selectable integer number of clock cycles.

10. The system of claim 1, including an analog signal delay module effective to delay outputs derived from one or more of the preamplifiers in a manner which enables the outputs from the preamplifiers to be synchronized.

11. The system of claim 10, wherein the analog signal delay module comprises a delay line with taps, wherein a desired tap is selected by a switch to obtain a desired delay.

12. The system of claim 10, wherein the analog signal delay module comprises delay filter elements that are switchable in and out of the signal path as needed.

13. The system of claim 10, wherein the analog signal delay module comprises an adjustable variable element that is controlled by a voltage controlled component.

14. The system of claim 1, wherein the selection circuit is coupled to respective overflow signals provided by respective ones of said analog to digital converters.

15. The system of claim 1, wherein the selection circuit is coupled to a plurality of magnitude comparators which are respectively coupled to respective ones of said analog to digital converters, wherein each of said magnitude comparators is structured to compare an output of a respective analog to digital converter thereof to a respective predetermined reference, said selection circuit being responsive to said magnitude comparators to determine, in advance, whether one or more of said analog to digital converters is tending toward an erroneous reading.

16. The system of claim 1, wherein each of the analog to digital converters has a respective overflow output, and the selection circuit including a channel select logic circuit which receives the respective overflow output and selects the digitized signal of the analog to digital converters which provides the largest amplification without having overflowed.

17. An object inspection system, comprising:
a transmit and receive section to generate a test signal and to receive a responsive echo signal;
a transducer that converts the test signal to an ultrasonic signal, applies the ultrasonic signal to a target object to be tested, receives an ultrasonic echo signal and produces the echo signal for the transmit and receive section;
a signal processing circuit coupled with the transmit and receive section for receiving and processing the echo signal, the signal processing circuit including at least two signal processing channels, each channel scaling the echo signal to a different degree, and each channel having a respective analog to digital converter which outputs a respective digitized signal;
a selection circuit which selects an output of the respective analog to digital converter which provides the largest amplification of the echo signal without having overflowed; and
a first one of said signal processing channels being coupled directly to the echo signal and comprising a respective preamplifier and a respective clamping circuit for preventing said preamplifier from becoming saturated, and a second one of said signal processing channels being coupled directly to the echo signal and comprising a respective preamplifier and a respective clamping circuit to prevent saturation of the preamplifier of the second one of said signal processing channels, the clamping circuit of the second signal processing channel being configured to maintain a constant input impedance on the echo signal, at least up to a signal level of said echo signal which equals a maximum input range to the preamplifier of the first one of said signal processing channels,
wherein each of the analog to digital converters has a respective overflow output, and the selection circuit including a channel select logic circuit which receives the respective overflow outputs and selects a digitized signal of the analog to digital converter which provides the largest amplification without having overflowed.

18. An object inspection system, comprising:
a transmit and receive section to generate a test signal and to receive a responsive echo signal;
a transducer that converts the test signal to an ultrasonic signal, applies the ultrasonic signal to a target object to be tested, receives an ultrasonic echo signal and produces the echo signal for the transmit and receive section;
a signal processing circuit coupled with the transmit and receive section for receiving and processing the echo signal, the signal processing circuit including at least two signal processing channels, each channel scaling the echo signal to a different degree, and each channel having a respective analog to digital converter which outputs a respective digitized signal;
a selection circuit which selects an output of the respective analog to digital converter which provides the largest amplification of the echo signal without having overflowed; and
a first one of said signal processing channels being coupled directly to the echo signal and comprising a respective preamplifier and a respective clamping circuit for preventing said preamplifier from becoming saturated, and a second one of said signal processing channels being coupled directly to the echo signal and comprising a respective preamplifier and a respective clamping circuit to prevent saturation of the preamplifier of the second one of said signal processing channels, the clamping circuit of the second signal processing channel being configured to maintain a constant input impedance on the echo signal, at least up to a signal level of said echo signal which equals a maximum input range to the preamplifier of the first one of said signal processing channels,
including a respective base line correction system associated with respective ones of one or more of said analog to digital converters, said base line correction systems being respectively coupled to a multiplexer which channels a selected one of the one or more of said analog to digital converters being processed.

* * * * *